(12) United States Patent
Famodu et al.

(10) Patent No.: US 6,255,090 B1
(45) Date of Patent: Jul. 3, 2001

(54) PLANT AMINOACYL-TRNA SYNTHETASE

(75) Inventors: Layo O. Famodu, Newark, DE (US); Emil M. Orozco, Jr., West Grove, PA (US); J. Antoni Rafalski, Wilmington, DE (US)

(73) Assignees: E. I. du Pont de Nemours & Company, Wilmington, DE (US); Pioneer Hi-Bred, INternational, Inc, Des Moines, IA (US)

( * ) Notice: Subject to any disclaimer, the term of this patent is extended or adjusted under 35 U.S.C. 154(b) by 0 days.

(21) Appl. No.: 09/352,990

(22) Filed: Jul. 14, 1999

Related U.S. Application Data

(60) Provisional application No. 60/092,866, filed on Jul. 15, 1998.

(51) Int. Cl.$^7$ .................................................. C12N 9/00
(52) U.S. Cl. ................... 435/183; 435/320.1; 435/325; 435/254.11; 435/252.3; 435/419; 536/23.1; 536/23.2; 800/278; 800/285; 800/286; 800/295
(58) Field of Search ................... 536/23.2, 23.1; 435/419, 252.3, 254.11, 6, 325, 183, 320.1; 800/295, 278, 285, 286

(56) References Cited

PUBLICATIONS

Neidhart et al. (1975) Annu. Rev. Microbiol. 29:215–250.
Zon et al. (1988) Phytochemistry 27(3):711–714.
Heacock et al. (1996) Bioorganic Chemistry 24(3):273–289.
GenBank Accession No: AAD21582.
Mol. Gen. Genet. 261(1), 142–151 (1999).
GenBank Accession No: P15178.
J. Biol. Chem. 264(2),842–847 (1989).
Gene 180 (1–2), 197–205 (1996).
GenBank Accession No: NP–001340.
J. Biol. Chem. 264, 16608–16612(1989).
J. Biol. Chem. 268(9), 6014–6023 (1993).
GenBank Acession No: P43816.
Science 269 (5223), 496–512 (1995).
GenBank Accession No: CAA39691.
Nucleic Acids Res. 19(2), 265–269 (1991).
GenBank Accession No: P73655.
DNA Res. 3(3), 109–136 (1996).
GenBank Accession No: P04077.
Biochemistry 25(8), 1887–1891.
GenBank Accession No. J04487 (Apr. 1993).*
GenBank Accession Number T23387 (Jul. 1994).*
GenBank Accession Number AA749675 (Jan. 1998).*

\* cited by examiner

*Primary Examiner*—Ponnathapu Achutamurthy
*Assistant Examiner*—Kathleen Kerr

(57) ABSTRACT

This invention relates to an isolated nucleic acid fragment encoding an aminoacyl-tRNA synthetase. The invention also relates to the construction of a chimeric gene encoding all or a portion of the aminoacyl-tRNA synthetase, in sense or antisense orientation, wherein expression of the chimeric gene results in production of altered levels of the aminoacyl-tRNA synthetase in a transformed host cell.

16 Claims, No Drawings

SEQUENCE LISTING

<160> NUMBER OF SEQ ID NOS: 29

<210> SEQ ID NO 1
<211> LENGTH: 1948
<212> TYPE: DNA
<213> ORGANISM: Zea mays

<400> SEQUENCE: 1

```
cgcacgatag ccgccgccgt cgaccagagc actcccccgt cgtcgccacg atgtcgtctg      60
agcctccacc cgcctcctct gccgccgccg gagaggaact cgctgctgac ctttccgccg     120
ctaccctcag caagaagcag cagaagaagg acgcgaggaa ggcggagaag gcagagcagc     180
gccagcgtca gcagcagcag cagcagcagc cggcggacgc cgaggacccg ttcgcggcca     240
actacggcga ggtccccgtc gaggagatcc agtcaaaggc catctccggc cgctcgtggt     300
cccatgtcgg cgacctcgac gactccgctg cgggccgctc cgtgcttatc cgcggagccg     360
cgcaggccat ccgtccggtc agcaagaaga tggctttcgt cgtgctgcgc cagagtatga     420
gcaccgtgca gtgcgtgctc gtcgccagcg ccgacgccgg cgtcagcacg cagatggtgc     480
gcttcgccac cgccctcagc aaggagtcca tcgtcgacgt tgagggcgtc gtctccctcc     540
caaaggagcc cctcaaggcc accacacagc aggttgagat ccaagtgagg aagatctatt     600
gcatcaatag ggctattccg acccttccaa ttaaccttga agatgcggct cggagtgagg     660
cagattttga gaaggctgaa ttggctggag aaaagcttgt tcgcgttggc caagataccc     720
gcttgaacta cagagctatt gatctacgaa caccctcgaa tcaagccata ttccggatcc     780
agtgtcaagt tgaaaacaaa tttagagatt ttttgttgtc gaagaacttt gtcgggatcc     840
```

-continued

```
acaccccaaa attgatttct ggatctagtg aaggggggtgc ggctgtattc aagcttctgt     900
acaatggtca acctgcttgt ttggcacaat cccctcagtt atacaagcaa atggctatct     960
ctggtggttt tgagcgagta tttgaggtcg gccctgtgtt tagagcagaa aattcaaaca    1020
cacacaggca tctatgtgag ttcgttggtc ttgatgctga aatggagatt aaggagcatt    1080
attttgaggt ctgtgacatt atagatggct tattcgtatc aatatttaaa cacttgtctg    1140
aaaactgcaa gaaagaactc gaatcaataa acaggcagta tccatttgaa cctctgaagt    1200
atctagacaa aacctttaag ctcacttatg aagaaggaat tcaaatgttg aaggaagccg    1260
gaacagaaat cgagcctatg ggtgacctca ataccgaagc tgagaaaaaa cttggtcggc    1320
ttgtcaggga aaagtatgac acagattttt tcatcctgta tcggtatcct ttggctgtac    1380
gtccgttcta caccatgcct tgttatgaca acccagcgta caccaattct tttgatgtct    1440
tcattcgagg cgaggagata atatctggag cacaaaggat acacactcct gagctgctgg    1500
ccaagcgcgc gacagagtgt ggaatcgacg tgagcactat ctcggcctac attgaatcct    1560
tcagctatgg cgtgccgcca cacggcggtt tcggggtggg tttggagagg gtggtgatgc    1620
tgttctgtgc cctgaacaac atcaggaaga cctccctgtt cccgcgcgac ccgcagaggc    1680
tcgtgccgta agtttctgat tccaagcctg agtcttcgag tggtctacgg agcagatccg    1740
atgttgttac catcagagtt gacttgcaat cttagctcct gaacctggcg gttaccgtgg    1800
atcagagttc ctgttgaatt tcacaaaagc ctacttgttc ctaatagatt gctgcaacca    1860
acaatattac gacccctttcg ggcttttctt cccgcctcac gtgttattct ggtctatact    1920 tgttttttaag tgcaagtatt gctcagtt                                       1948
```

<210> SEQ ID NO 2
<211> LENGTH: 546
<212> TYPE: PRT
<213> ORGANISM: Zea mays

<400> SEQUENCE: 2

Met Ser Ser Glu Pro Pro Ala Ser Ala Ala Gly Glu Glu
 1               5                  10              15

Leu Ala Ala Asp Leu Ser Ala Ala Thr Leu Ser Lys Lys Gln Gln Lys
                20                  25                  30

Lys Asp Ala Arg Lys Ala Glu Lys Ala Glu Gln Arg Gln Arg Gln
            35                  40                  45

Gln Gln Gln Gln Gln Pro Ala Asp Ala Glu Asp Pro Phe Ala Ala Asn
        50                  55                  60

Tyr Gly Glu Val Pro Val Glu Glu Ile Gln Ser Lys Ala Ile Ser Gly
 65                 70                  75                  80

Arg Ser Trp Ser His Val Gly Asp Leu Asp Asp Ser Ala Ala Gly Arg
                85                  90                  95

Ser Val Leu Ile Arg Gly Ala Ala Gln Ala Ile Arg Pro Val Ser Lys
            100                 105                 110

Lys Met Ala Phe Val Val Leu Arg Gln Ser Met Ser Thr Val Gln Cys
        115                 120                 125

Val Leu Val Ala Ser Ala Asp Ala Gly Val Ser Thr Gln Met Val Arg
    130                 135                 140

Phe Ala Thr Ala Leu Ser Lys Glu Ser Ile Val Asp Val Glu Gly Val
145                 150                 155                 160

Val Ser Leu Pro Lys Glu Pro Leu Lys Ala Thr Thr Gln Gln Val Glu
                165                 170                 175

```
Ile Gln Val Arg Lys Ile Tyr Cys Ile Asn Arg Ala Ile Pro Thr Leu
            180                 185                 190

Pro Ile Asn Leu Glu Asp Ala Ala Arg Ser Glu Ala Asp Phe Glu Lys
            195                 200                 205

Ala Glu Leu Ala Gly Glu Lys Leu Val Arg Val Gly Gln Asp Thr Arg
210                 215                 220

Leu Asn Tyr Arg Ala Ile Asp Leu Arg Thr Pro Ser Asn Gln Ala Ile
225                 230                 235                 240

Phe Arg Ile Gln Cys Gln Val Glu Asn Lys Phe Arg Asp Phe Leu Leu
            245                 250                 255

Ser Lys Asn Phe Val Gly Ile His Thr Pro Lys Leu Ile Ser Gly Ser
            260                 265                 270

Ser Glu Gly Gly Ala Ala Val Phe Lys Leu Leu Tyr Asn Gly Gln Pro
            275                 280                 285

Ala Cys Leu Ala Gln Ser Pro Gln Leu Tyr Lys Gln Met Ala Ile Ser
            290                 295                 300

Gly Gly Phe Glu Arg Val Phe Glu Val Gly Pro Val Phe Arg Ala Glu
305                 310                 315                 320

Asn Ser Asn Thr His Arg His Leu Cys Glu Phe Val Gly Leu Asp Ala
            325                 330                 335

Glu Met Glu Ile Lys Glu His Tyr Phe Glu Val Cys Asp Ile Ile Asp
            340                 345                 350

Gly Leu Phe Val Ser Ile Phe Lys His Leu Ser Glu Asn Cys Lys Lys
            355                 360                 365

Glu Leu Glu Ser Ile Asn Arg Gln Tyr Pro Phe Glu Pro Leu Lys Tyr
            370                 375                 380

Leu Asp Lys Thr Phe Lys Leu Thr Tyr Glu Glu Gly Ile Gln Met Leu
385                 390                 395                 400

Lys Glu Ala Gly Thr Glu Ile Glu Pro Met Gly Asp Leu Asn Thr Glu
            405                 410                 415

Ala Glu Lys Lys Leu Gly Arg Leu Val Arg Glu Lys Tyr Asp Thr Asp
            420                 425                 430

Phe Phe Ile Leu Tyr Arg Tyr Pro Leu Ala Val Arg Pro Phe Tyr Thr
            435                 440                 445

Met Pro Cys Tyr Asp Asn Pro Ala Tyr Thr Asn Ser Phe Asp Val Phe
            450                 455                 460

Ile Arg Gly Glu Glu Ile Ile Ser Gly Ala Gln Arg Ile His Thr Pro
465                 470                 475                 480

Glu Leu Leu Ala Lys Arg Ala Thr Glu Cys Gly Ile Asp Val Ser Thr
            485                 490                 495

Ile Ser Ala Tyr Ile Glu Ser Phe Ser Tyr Gly Val Pro Pro His Gly
            500                 505                 510

Gly Phe Gly Val Gly Leu Glu Arg Val Val Met Leu Phe Cys Ala Leu
            515                 520                 525

Asn Asn Ile Arg Lys Thr Ser Leu Phe Pro Arg Asp Pro Gln Arg Leu
            530                 535                 540

Val Pro
545

<210> SEQ ID NO 3
<211> LENGTH: 730
<212> TYPE: DNA
<213> ORGANISM: Oryza sativa

<400> SEQUENCE: 3
```

```
gcacgagctt acacggcacg agcttacagg aattcaaatg ctgaaggaag ctggaacaga      60
aatcgaaccc atgggtgacc tcaacactga agctgagaaa aaactaggcc ggcttgttaa     120
ggagaagtat ggaacagaat ttttcatcct ctatcggtat cctttggctg tgcgtccctt     180
ctacaccatg ccttgttatg caacccagc ttacagtaac tcttttgatg tctttattcg      240
aggagaggaa ataatatctg gagcacaaag aatacattta ccagagctat tgacgaaacg     300
tgcaacagag tgtggaattg atgcgagtac tatttcatca tatatcgaat cgttcagcta     360
tggtgcacct cctcatggtg gttttggtgt cggcctggag agggtggtaa tgctgttctg     420
cgccctaaac aacatcagga agacatcact tttccctcgc gatccacaaa ggctggtgcc     480
ataatttgct ttttttccca agagcaaggt ttggactcag tacggactgg gcagttttcc     540
tcggctggtt tttttacctg gacattattt tcgtatttat taatgtgctg tactgcaaaa     600
gctgctcctt tccacaacat ttggaatagt tgccgataca tttggaatag gctcaacgt      660
tggcgttgtg atttcgttga tgatcccgct attcgtaaca aaaaaaaaaa aaaaaaaaaa     720
aaaaaaaaaa                                                            730

<210> SEQ ID NO 4
<211> LENGTH: 148
<212> TYPE: PRT
<213> ORGANISM: Oryza sativa

<400> SEQUENCE: 4

Met Leu Lys Glu Ala Gly Thr Glu Ile Glu Pro Met Gly Asp Leu Asn
 1               5                  10                  15

Thr Glu Ala Glu Lys Lys Leu Gly Arg Leu Val Lys Glu Lys Tyr Gly
            20                  25                  30

Thr Glu Phe Phe Ile Leu Tyr Arg Tyr Pro Leu Ala Val Arg Pro Phe
        35                  40                  45

Tyr Thr Met Pro Cys Tyr Asp Asn Pro Ala Tyr Ser Asn Ser Phe Asp
    50                  55                  60

Val Phe Ile Arg Gly Glu Glu Ile Ile Ser Gly Ala Gln Arg Ile His
65                  70                  75                  80

Leu Pro Glu Leu Leu Thr Lys Arg Ala Thr Glu Cys Gly Ile Asp Ala
                85                  90                  95

Ser Thr Ile Ser Ser Tyr Ile Glu Ser Phe Ser Tyr Gly Ala Pro Pro
            100                 105                 110

His Gly Gly Phe Gly Val Gly Leu Glu Arg Val Val Met Leu Phe Cys
        115                 120                 125

Ala Leu Asn Asn Ile Arg Lys Thr Ser Leu Phe Pro Arg Asp Pro Gln
    130                 135                 140

Arg Leu Val Pro
145

<210> SEQ ID NO 5
<211> LENGTH: 1109
<212> TYPE: DNA
<213> ORGANISM: Glycine max

<400> SEQUENCE: 5
gcacgaggtc atcagagaga atggcttcac cgttcaatgc ttggtgcagg cgcaggccga      60
tacggtgagc ccgcagatgg tgaagttcgc cgctgcactc agccgcgagt ccatcgtcga     120
tgtcgaaggc gttgtttcga tcccctccgc tcccatcaaa ggcgccacac aacaggtgga     180
```

-continued

```
aattcaagtg aggaagttgt attgtgtcag tagggctgta cctactctgc ctattaatct    240
tgaggatgct gctcgaagtg aagttgaaat cgagacggct cttcaggctg gtgagcaact    300
tgttcgtgtt aatcaggata cacgtctgaa cttagggtg cttgatgtgc aacgccagc     360 taatcaaggg attttccgca ttcagtctca agttggaaat gcgtttagac aattcttatt    420
atctgaaggt ttttgtgaaa tccacactcc aaagttgata gctggatcta gtgagggagg    480
agctgctgtt tttagactgg actacaaagg tcaacctgca tgcctggccc agtcacctca    540
gcttcacaag caaatgtcta tttgtggaga ttttggccgt gtttttgaga ttggtcctgt    600
gtttagagca gaagattcct acactcacag gcatctgtgt gagtttacag gtcttgatgt    660
tgaaatggag attaagaagc attactttga ggttatggat atagtcgata gattgtttgt    720
cgcaatgttt gacagtttga accagaattg taagaaggat ctggaagctg tcgggtctca    780
gtatccattt gaacctttga gtatctgcg gacgacacta cggcttacat atgaagaagg    840
gattcagatg ctcaaggatg ttggagtaga aattgaacct tatggtgact tgaatactga    900
agcggaaagg aaattgggtc agctagtctc agagaaatat ggcacagagt tctatatcct    960
tcaccggtac cctttggctg taaggccatt ctatacaatg ccttgctacg acaatcctgc   1020
atacagcaac tcgtttgatg tctttattcg aggtgaggag ataatttcag gagctcagcg   1080
tgttcatgtg ccagaatttt tggaacaag                                    1109
```

<210> SEQ ID NO 6
<211> LENGTH: 369
<212> TYPE: PRT
<213> ORGANISM: Glycine max

<400> SEQUENCE: 6

```
His Glu Val Ile Arg Glu Asn Gly Phe Thr Val Gln Cys Leu Val Gln
  1               5                  10                  15

Ala Gln Ala Asp Thr Val Ser Pro Gln Met Val Lys Phe Ala Ala Ala
             20                  25                  30

Leu Ser Arg Glu Ser Ile Val Asp Val Glu Gly Val Val Ser Ile Pro
         35                  40                  45

Ser Ala Pro Ile Lys Gly Ala Thr Gln Gln Val Glu Ile Gln Val Arg
     50                  55                  60

Lys Leu Tyr Cys Val Ser Arg Ala Val Pro Thr Leu Pro Ile Asn Leu
 65                  70                  75                  80

Glu Asp Ala Ala Arg Ser Glu Val Glu Ile Thr Ala Leu Gln Ala
             85                  90                  95

Gly Glu Gln Leu Val Arg Val Asn Gln Asp Thr Arg Leu Asn Phe Arg
            100                 105                 110

Val Leu Asp Val Arg Thr Pro Ala Asn Gln Gly Ile Phe Arg Ile Gln
        115                 120                 125

Ser Gln Val Gly Asn Ala Phe Arg Gln Phe Leu Leu Ser Glu Gly Phe
    130                 135                 140

Cys Glu Ile His Thr Pro Lys Leu Ile Ala Gly Ser Ser Glu Gly Gly
145                 150                 155                 160

Ala Ala Val Phe Arg Leu Asp Tyr Lys Gly Gln Pro Ala Cys Leu Ala
                165                 170                 175

Gln Ser Pro Gln Leu His Lys Gln Met Ser Ile Cys Gly Asp Phe Gly
            180                 185                 190

Arg Val Phe Glu Ile Gly Pro Val Phe Arg Ala Glu Asp Ser Tyr Thr
        195                 200                 205
```

```
His Arg His Leu Cys Glu Phe Thr Gly Leu Asp Val Glu Met Glu Ile
    210                 215                 220
Lys Lys His Tyr Phe Glu Val Met Asp Ile Val Asp Arg Leu Phe Val
225                 230                 235                 240
Ala Met Phe Asp Ser Leu Asn Gln Asn Cys Lys Lys Asp Leu Glu Ala
                245                 250                 255
Val Gly Ser Gln Tyr Pro Phe Pro Leu Lys Tyr Leu Arg Thr Thr
            260                 265                 270
Leu Arg Leu Thr Tyr Glu Glu Gly Ile Gln Met Leu Lys Asp Val Gly
            275                 280                 285
Val Glu Ile Glu Pro Tyr Gly Asp Leu Asn Thr Glu Ala Glu Arg Lys
        290                 295                 300
Leu Gly Gln Leu Val Ser Glu Lys Tyr Gly Thr Glu Phe Tyr Ile Leu
305                 310                 315                 320
His Arg Tyr Pro Leu Ala Val Arg Pro Phe Tyr Thr Met Pro Cys Tyr
                325                 330                 335
Asp Asn Pro Ala Tyr Ser Asn Ser Phe Asp Val Phe Ile Arg Gly Glu
            340                 345                 350
Glu Ile Ile Ser Gly Ala Gln Arg Val His Val Pro Glu Phe Leu Glu
        355                 360                 365
Gln
```

<210> SEQ ID NO 7
<211> LENGTH: 836
<212> TYPE: DNA
<213> ORGANISM: Triticum aestivum

<400> SEQUENCE: 7

```
tacacatgca gactttcagt gagttttttgt tctcggactt gggatccaca gtccaaagtt    60
gattggtgga tcaagtgaac ttggtgcatc tccattcaag ctggcgtaca attaccaacc   120
tgcttattta gcgcagtctc tacaatcata caagcaaatg agcatctgtg gtggctttgg   180
gcgcgtgttt gaggctggtc cggtatttag atcagaaaaa tcaaacactc acaggcatct   240
atgtgagttt attgggttgg atgcagaaat ggagattaag gagcactact ttgaggtttg   300
tgatatcata gattgctaat tgtagcaata ttcaaacacc caaatgaaaa ttgtcagaag   360
gaactcgaga caataaatag gcagtatcca tttgaacctc tgaagtacct agagaaaacg   420
ttgaagctaa cgtacgagga agggattaaa atgctcaagg tttcattctg gaatcctcta   480
ggcagggtgc ttgcaatccc ctacatctcg gctgcaacaa aaaagaccca acgaggctgt   540
tgtttcaagc tcagaccctc ttcattgcac gcggtgctag aaggagaact gggttgtggt   600
gctgttgctg gtcgttttcc ttttttacttt tgcactttgg ccgtcataaa cgatacatgc   660
ttgctccctg gatggatctc tttctctccc tggatctttt aaacaggtgt tgtgattaaa   720
attgtgataa atcagtgttc atcactaaaa aaaaaaaaa aaaaaaaaa aaaaaaaaa    780
aatctcgagg gggggcccgg tactgttcac cgcgtggcgc cgggctagag actagt        836
```

<210> SEQ ID NO 8
<211> LENGTH: 98
<212> TYPE: PRT
<213> ORGANISM: Triticum aestivum

<400> SEQUENCE: 8

```
Val Phe Val Leu Gly Leu Gly Ile His Ser Pro Lys Leu Ile Gly Gly
  1               5                  10                  15
```

```
Ser Ser Glu Leu Gly Ala Ser Pro Phe Lys Leu Ala Tyr Asn Tyr Gln
            20                  25                  30

Pro Ala Tyr Leu Ala Gln Ser Leu Gln Ser Tyr Lys Gln Met Ser Ile
        35                  40                  45

Cys Gly Gly Phe Gly Arg Val Phe Glu Ala Gly Pro Val Phe Arg Ser
    50                  55                  60

Glu Lys Ser Asn Thr His Arg His Leu Cys Glu Phe Ile Gly Leu Asp
65                  70                  75                  80

Ala Glu Met Glu Ile Lys Glu His Tyr Phe Glu Val Cys Asp Ile Ile
                85                  90                  95

Asp Cys

<210> SEQ ID NO 9
<211> LENGTH: 2085
<212> TYPE: DNA
<213> ORGANISM: Zea mays

<400> SEQUENCE: 9
ggaaaccgtg tttcgacggg ccgcagtggg cagtggcttg gcccatcgaa cccacttgcc      60
actcacttcc acctgaactt tgccctgcct tctctcgacg actcccctgt ccccgccgcc     120
gccgccgccg caaatcccct tccgcgtctg tctggcctct ggggcttcta ggttagcgcg     180
tgcgaccacc atggccgagg aggtccaggc tccactttcc gccaccatgg cgaaggaggc     240
ccagtcgccg ccgtccgcaa ccatagcgga ggcgacggcg ccgccgcagc tcttattatt     300
taactccttt acgaagaggg aggagccatt ccagccccgg gtagagggga aggtagggat     360
gtacgtctgt ggcgtcactc cctacgactt tagccacatc ggccacgcgc gtgcctacgt     420
cgccttcgac gtcctctaca ggtaccttaa attcttgggg tatgaagttg aatatgtccg     480
taatttcacg gatattgatg acaagattat taagcgtgcc aatgaacgcg gtgaaacagt     540
aacaagcttg agtagccagt ttatcaatga atttcttctt gacatgactg agctccagtg     600
cttgcctcct acctgcgagc cacgggtaac agaacacatt gagcatatta aaagttgat       660
aacacagata atggagaatg gcaaagccta tgctattgaa ggagatgttt actttttcagt     720
tgaaagtttt cctgaatatc tcagtttatc tggaagaaaa tttgatcaaa atcaggcagg     780
tgcacgggtt gcttttgata caagaaagcg taatcctgca gacttcgcac tctggaaagc     840
tgcaaaggag ggtgaacctt tttgggatag ccctttgggc cgtggaagac caggttggca     900
tattgaatgc agcgcaatga gtgctcacta tttaggacat gtattcgata ttcatggtgg     960
ggggaaagat ttgatttttc ctcatcatga gaatgagctt gcacaaagcc gcgcagctta    1020
tcctgatagc gaggtcaaat gctggatgca caatggcttt gttaacaagg atgataaaaa    1080
aatggcaaaa tcagataata acttttttcac gattagagat atcattgctc tttaccatcc    1140
aatggcttta agattttttct tgatgcgcac acattataga tcagtgttaa ccattctga    1200
tcaagcgctt gagattgcat ctgatcgtgt ctactacatt tatcagactc tatatgactg    1260
tgaggaagtg ttagctacat atcgtgaaga gggtacctct ctcccagtgc cgtctgagga    1320
gcaaaatctg attggtaagc accattcaga attcttgaaa catatgtcga atgatcttaa    1380
aaccacagat gttctggacc gttgcttcat ggagctgctg aaggccataa acagcagtct    1440
gaatgatttg aagaaactgc agcaaaaaat agaacagcaa aagaagaaac agcaacagca    1500
gaagaagcag caacagcaga agcagcagca acagaagcaa cagcaattgc aaaaacagcc    1560
agaagattat attcaagctc tgattgcact ggaaacagaa cttaaaaaca aattgtctat    1620
```

-continued

```
acttggtctg atgccatctt catctttggc agaggtactg aagcaattga aggacaaatc    1680
attaaagcga gcagggctga ctgaagaaca attgcaagag cagattgagc agagaaatgt    1740
cgcaaggaag aataagcagt ttgagatatc tgatggaatc aggaaaaacc ttgctaccaa    1800
aggcatcgcc ctgatggacg aaccttctgg tacagtatgg agaccatgcg aaccagagcg    1860
gtctgaaagg tcatgattag ctcactgact caacaagtga tggcggtgta aaatgagatt    1920
tttgcctgag ggcagttatc gcattttgaa gactaacaaa aatcgccatc tctggatgtg    1980
gtattctaca gggtaggggt tccaggttga ctcaccagtt aaaacatgca tttctggttg    2040
tataacaagc aatgaacccc atatatatac ttgacagttg actcc                    2085
```

<210> SEQ ID NO 10
<211> LENGTH: 599
<212> TYPE: PRT
<213> ORGANISM: Zea mays

<400> SEQUENCE: 10

```
Thr Leu Pro Cys Leu Leu Ser Thr Thr Pro Leu Ser Pro Pro Pro Pro
 1               5                  10                  15

Pro Pro Gln Ile Pro Phe Arg Val Cys Leu Ala Ser Gly Ala Ser Arg
            20                  25                  30

Leu Ala Arg Ala Thr Thr Met Ala Glu Glu Val Gln Ala Pro Leu Ser
        35                  40                  45

Ala Thr Met Ala Lys Glu Ala Gln Ser Pro Pro Ser Ala Thr Ile Ala
    50                  55                  60

Glu Ala Thr Ala Pro Pro Gln Leu Leu Leu Phe Asn Ser Phe Thr Lys
65                  70                  75                  80

Arg Glu Glu Pro Phe Gln Pro Arg Val Glu Gly Lys Val Gly Met Tyr
                85                  90                  95

Val Cys Gly Val Thr Pro Tyr Asp Phe Ser His Ile Gly His Ala Arg
            100                 105                 110

Ala Tyr Val Ala Phe Asp Val Leu Tyr Arg Tyr Leu Lys Phe Leu Gly
        115                 120                 125

Tyr Glu Val Glu Tyr Val Arg Asn Phe Thr Asp Ile Asp Asp Lys Ile
    130                 135                 140

Ile Lys Arg Ala Asn Glu Arg Gly Glu Thr Val Thr Ser Leu Ser Ser
145                 150                 155                 160

Gln Phe Ile Asn Glu Phe Leu Leu Asp Met Thr Glu Leu Gln Cys Leu
                165                 170                 175

Pro Pro Thr Cys Glu Pro Arg Val Thr Glu His Ile Glu His Ile Ile
            180                 185                 190

Lys Leu Ile Thr Gln Ile Met Glu Asn Gly Lys Ala Tyr Ala Ile Glu
        195                 200                 205

Gly Asp Val Tyr Phe Ser Val Glu Ser Phe Pro Glu Tyr Leu Ser Leu
    210                 215                 220

Ser Gly Arg Lys Phe Asp Gln Asn Gln Ala Gly Ala Arg Val Ala Phe
225                 230                 235                 240

Asp Thr Arg Lys Arg Asn Pro Ala Asp Phe Ala Leu Trp Lys Ala Ala
                245                 250                 255

Lys Glu Gly Glu Pro Phe Trp Asp Ser Pro Trp Gly Arg Gly Arg Pro
            260                 265                 270

Gly Trp His Ile Glu Cys Ser Ala Met Ser Ala His Tyr Leu Gly His
        275                 280                 285

Val Phe Asp Ile His Gly Gly Gly Lys Asp Leu Ile Phe Pro His His
```

```
                        290                 295                 300
Glu Asn Glu Leu Ala Gln Ser Arg Ala Ala Tyr Pro Asp Ser Glu Val
305                 310                 315                 320

Lys Cys Trp Met His Asn Gly Phe Val Asn Lys Asp Asp Lys Lys Met
                325                 330                 335

Ala Lys Ser Asp Asn Asn Phe Phe Thr Ile Arg Asp Ile Ile Ala Leu
                340                 345                 350

Tyr His Pro Met Ala Leu Arg Phe Phe Leu Met Arg Thr His Tyr Arg
                355                 360                 365

Ser Asp Val Asn His Ser Asp Gln Ala Leu Glu Ile Ala Ser Asp Arg
                370                 375                 380

Val Tyr Tyr Ile Tyr Gln Thr Leu Tyr Asp Cys Glu Glu Val Leu Ala
385                 390                 395                 400

Thr Tyr Arg Glu Glu Gly Thr Ser Leu Pro Val Pro Ser Glu Glu Gln
                405                 410                 415

Asn Leu Ile Gly Lys His His Ser Glu Phe Leu Lys His Met Ser Asn
                420                 425                 430

Asp Leu Lys Thr Thr Asp Val Leu Asp Arg Cys Phe Met Glu Leu Leu
                435                 440                 445

Lys Ala Ile Asn Ser Ser Leu Asn Asp Leu Lys Lys Leu Gln Gln Lys
                450                 455                 460

Ile Glu Gln Gln Lys Lys Gln Gln Gln Lys Gln Gln Gln
465                 470                 475                 480

Gln Lys Gln Gln Gln Gln Lys Gln Gln Gln Leu Gln Lys Gln Pro Glu
                485                 490                 495

Asp Tyr Ile Gln Ala Leu Ile Ala Leu Glu Thr Glu Leu Lys Asn Lys
                500                 505                 510

Leu Ser Ile Leu Gly Leu Met Pro Ser Ser Leu Ala Glu Val Leu
                515                 520                 525

Lys Gln Leu Lys Asp Lys Ser Leu Lys Arg Ala Gly Leu Thr Glu Glu
                530                 535                 540

Gln Leu Gln Glu Gln Ile Glu Gln Arg Asn Val Ala Arg Lys Asn Lys
545                 550                 555                 560

Gln Phe Glu Ile Ser Asp Gly Ile Arg Lys Asn Leu Ala Thr Lys Gly
                565                 570                 575

Ile Ala Leu Met Asp Glu Pro Ser Gly Thr Val Trp Arg Pro Cys Glu
                580                 585                 590

Pro Glu Arg Ser Glu Glu Ser
                595

<210> SEQ ID NO 11
<211> LENGTH: 1957
<212> TYPE: DNA
<213> ORGANISM: Oryza sativa

<400> SEQUENCE: 11
cgccagttct agggttagct cgtcggcgtc cagccctctc actctccccc tccgctctca      60
cgatggcgga gagcgcgaag ccgacgccgc agctggagct cttcaactcg atgacgaaga     120
agaaggagct cttcgagccg cttgtggagg ggaaggtccg catgtatgtg tgcggcgtca     180
cgccctacga cttcagccac atcggccacg cccgcgccta cgtcgccttc gacgtcctct     240
acaggtatct taaattcttg gggtacgagg tcgaatatgt gcgcaacttc actgatattg     300
atgacaagat tatcaaacga gcaaatgaag ctggtgaaac tgtaactagc ttgagcagcc     360
```

-continued

```
ggtttattaa tgaattcctt ctcgatatgg ctcagctcca gtgcttaccc ccaacttgtg      420
agccacgtgt gacggatcac attgaacata ttatagagtt gataaccaag ataatggaga      480
atgggaaagc ctatgctatg gaaggagatg tttactttc agttgatact ttccctgagt       540
atctcagttt atctggaagg aagttagatc ataatcttgc tggttcgcgg gttgctgtcg      600
atacaagaaa gcggaaccct gcagactttg cgctgtggaa ggctgctaag gaaggcgaac      660
ctttctggga tagcccatgg ggccgtggta gaccaggatg gcatattgaa tgcagtgcaa      720
tgagtgctca ttatttagga catgtgtttg atatccatgg tggagggaaa gatctgatat      780
ttcctcatca tgagaatgag cttgctcaga gccgggcagc ttatccagaa agtgaggtca      840
aatgttggat gcacaatggg tttgttaaca aggatgatca gaaaatgtca aagtcagata      900
aaaatttctt cacaatccga gatattattg atctgtacca tcccatggct ttgaggtttt      960
tcctgatgcg cacacattac agaggagatg tgaatcactc tgacaaagca cttgagatag     1020
catctgatcg tgtctactac atatatcaga ctttatatga ctgtgaggaa gtgttgtctc     1080
aatatcgtgg agagaatatc tctgtcccgg tccctgttga ggaacaagat atggttaaca     1140
agcaccattc agaattcttg gaatctatgg cggatgatct tagaacaaca gatgttctgg     1200
atggctttac tgacttgctg aaggcaatta acagcaattt gaatgatttt aagaagttgc     1260
aacagaagct agagcagcaa aagaagaaac aacaacagca gaagcagcag aagcaaaagc     1320
agcagcaggc acagaaacaa ccagaagaat atattcaagc tatgtttgca cttgagacag     1380
aaattaaaaa taaaatatct atccttggtc tgatgccacc ttcttcctg gcagaggcac      1440 tgaagcaact taaggataaa gctttgaaga gagcagggtt gactgaagaa ctgttgcagg     1500
agcaaattga gcagagaact gctgcaagga aaaacaagca gtttgatgtg tctgaccaaa     1560
tcaggaaaca gctaggcagc aaaggcatag ccctcatgga tgaacctact ggtacagtat     1620
ggagaccatg cgagccagag tctgaatagt cacatgattg atttgtgctt tggttaacag     1680
gtgatggtac aaactggaaa atttaaccaa gcacatctgc tgaattggtg taaattgatg     1740
cagatcaaca ttttttttg taattttgta ggggtttaag ttcactggcc aactgaaact      1800
tgcgtttctc gtggtgtaag aagcaaaacc ccatatactg atatactcga ggactcccctt    1860 gttggatgtt atgctttgga tttgaatatt gaagtcaaat cataattaca tttgcatgat     1920
caaaaaaaaa aaaaaaaaa aaaaaaaaa aaaaaa                                 1957
```

<210> SEQ ID NO 12
<211> LENGTH: 548
<212> TYPE: PRT
<213> ORGANISM: Oryza sativa

<400> SEQUENCE: 12

```
Pro Val Leu Gly Leu Ala Arg Arg Pro Ala Leu Ser Leu Ser Pro
  1               5                  10                 15

Ser Ala Leu Thr Met Ala Glu Ser Ala Lys Pro Thr Pro Gln Leu Glu
             20                  25                  30

Leu Phe Asn Ser Met Thr Lys Lys Glu Leu Phe Glu Pro Leu Val
         35                  40                  45

Glu Gly Lys Val Arg Met Tyr Val Cys Gly Val Thr Pro Tyr Asp Phe
     50                  55                  60

Ser His Ile Gly His Ala Arg Ala Tyr Val Ala Phe Asp Val Leu Tyr
 65                  70                  75                  80

Arg Tyr Leu Lys Phe Leu Gly Tyr Glu Val Glu Tyr Val Arg Asn Phe
                 85                  90                  95
```

-continued

```
Thr Asp Ile Asp Asp Lys Ile Ile Lys Arg Ala Asn Glu Ala Gly Glu
            100                 105                 110
Thr Val Thr Ser Leu Ser Ser Arg Phe Ile Asn Glu Phe Leu Leu Asp
            115                 120                 125
Met Ala Gln Leu Gln Cys Leu Pro Pro Thr Cys Glu Pro Arg Val Thr
            130                 135                 140
Asp His Ile Glu His Ile Ile Glu Leu Ile Thr Lys Ile Met Glu Asn
145                 150                 155                 160
Gly Lys Ala Tyr Ala Met Glu Gly Asp Val Tyr Phe Ser Val Asp Thr
                    165                 170                 175
Phe Pro Glu Tyr Leu Ser Leu Ser Gly Arg Lys Leu Asp His Asn Leu
            180                 185                 190
Ala Gly Ser Arg Val Ala Val Asp Thr Arg Lys Arg Asn Pro Ala Asp
            195                 200                 205
Phe Ala Leu Trp Lys Ala Ala Lys Glu Gly Glu Pro Phe Trp Asp Ser
            210                 215                 220
Pro Trp Gly Arg Gly Arg Pro Gly Trp His Ile Glu Cys Ser Ala Met
225                 230                 235                 240
Ser Ala His Tyr Leu Gly His Val Phe Asp Ile His Gly Gly Gly Lys
                    245                 250                 255
Asp Leu Ile Phe Pro His His Glu Asn Glu Leu Ala Gln Ser Arg Ala
            260                 265                 270
Ala Tyr Pro Glu Ser Glu Val Lys Cys Trp Met His Asn Gly Phe Val
            275                 280                 285
Asn Lys Asp Asp Gln Lys Met Ser Lys Ser Asp Lys Asn Phe Phe Thr
            290                 295                 300
Ile Arg Asp Ile Ile Asp Leu Tyr His Pro Met Ala Leu Arg Phe Phe
305                 310                 315                 320
Leu Met Arg Thr His Tyr Arg Gly Asp Val Asn His Ser Asp Lys Ala
                    325                 330                 335
Leu Glu Ile Ala Ser Asp Arg Val Tyr Tyr Ile Tyr Gln Thr Leu Tyr
            340                 345                 350
Asp Cys Glu Glu Val Leu Ser Gln Tyr Arg Gly Glu Asn Ile Ser Val
            355                 360                 365
Pro Val Pro Val Glu Glu Gln Asp Met Val Asn Lys His His Ser Glu
            370                 375                 380
Phe Leu Glu Ser Met Ala Asp Asp Leu Arg Thr Thr Asp Val Leu Asp
385                 390                 395                 400
Gly Phe Thr Asp Leu Leu Lys Ala Ile Asn Ser Asn Leu Asn Asp Phe
                    405                 410                 415
Lys Lys Leu Gln Gln Lys Leu Glu Gln Gln Lys Lys Gln Gln Gln
            420                 425                 430
Gln Lys Gln Gln Lys Gln Lys Gln Gln Ala Gln Lys Gln Pro Glu
            435                 440                 445
Glu Tyr Ile Gln Ala Met Phe Ala Leu Glu Thr Glu Ile Lys Asn Lys
            450                 455                 460
Ile Ser Ile Leu Gly Leu Met Pro Pro Ser Ser Leu Ala Glu Ala Leu
465                 470                 475                 480
Lys Gln Leu Lys Asp Lys Ala Leu Lys Arg Ala Gly Leu Thr Glu Glu
                    485                 490                 495
Leu Leu Gln Glu Gln Ile Glu Gln Arg Thr Ala Ala Arg Lys Asn Lys
            500                 505                 510
```

```
Gln Phe Asp Val Ser Asp Gln Ile Arg Lys Gln Leu Gly Ser Lys Gly
            515                 520                 525
Ile Ala Leu Met Asp Glu Pro Thr Gly Thr Val Trp Arg Pro Cys Glu
        530                 535                 540
Pro Glu Ser Glu
545
```

<210> SEQ ID NO 13
<211> LENGTH: 2183
<212> TYPE: DNA
<213> ORGANISM: Glycine max

<400> SEQUENCE: 13

| | | | | | |
|---|---|---|---|---|---|
| gcacgagata | aacgataacg | ttatttggct | gtgaatttgg | gatgagctgg | tccggtgcaa | 60 |
| aaatgggtac | ggtgtctctt | ctcaagtgct | acagacccctt | tttctctatg | cttttccctc | 120 |
| actccgctcc | acccagactc | cacgccgcca | tcttcaggag | caaaaacttt | tcttttttgcg | 180 |
| ccacctcgtc | cccgccgttg | acggcggaga | agggttgcgg | caaatccgac | gccgagtgtc | 240 |
| ccaccttgcc | ggaggtgtgg | ctgcacaaca | ccatgagtag | gacgaaggaa | ctcttcaaac | 300 |
| ccaaagtgga | atccaaagtg | ggaatgtacg | tgtgcggcgt | caccgcttat | gatcttagcc | 360 |
| atattggaca | cgctcgcgta | tacgtcaatt | tcgaccttct | ttacagatac | tttaagcatt | 420 |
| tgggatttga | agtctgttat | gttcgcaatt | tcactgacgt | agatgacaag | ataattgcta | 480 |
| gagcaaagga | gttaggagaa | gatccaatca | gtttgagctg | gcgctattgt | gaagagttct | 540 |
| gtcaagacat | ggtaactctt | aattgtctgt | ctccctctgt | ggaaccaaag | gtctcagagc | 600 |
| acatgcccca | aatcattgat | atgattgaga | agatccttaa | taatgggtat | gcctacattg | 660 |
| ttgatgggga | tgtgtacttt | aatgtagaaa | aatttccaga | atatgggaaa | ctatctagtc | 720 |
| gagatctaga | agataatcga | gctggtgaga | gggttgcagt | tgattctaga | aagaaaaatc | 780 |
| ctgctgattt | tgctctttgg | aagtctgcaa | agccagggga | gccattttgg | gagagtccct | 840 |
| ggggtcctgg | aagacctggg | tggcatattg | aatgcagtgc | catgagtgca | gcttatcttg | 900 |
| gttactcttt | tgatatccat | ggtggaggaa | tcgaccttgt | gtttcctcac | catgagaatg | 960 |
| aaattgctca | gagttgtgct | gcatgtaaga | aaagtgatat | aagtatatgg | atgcacaatg | 1020 |
| gttttgtcac | cattgactct | gtgaaaatgt | caaaatcttt | ggggaatttt | ttcacaatac | 1080 |
| gtcaggttat | agacgtttac | catccactgg | ccttgagata | ttttttgatg | agcgcacatt | 1140 |
| atcgatctcc | tattaactac | tcaaatatac | agctcgaaag | tgcttcagac | cgtgtttttt | 1200 |
| atatatatga | acattacat | gaatgtgaaa | gcttttgaa | tcagcatgat | cagaggaagg | 1260 |
| attccacccc | accggatact | ttggatatta | ttgataagtt | ccacgatgtt | ttttgacct | 1320 |
| caatgtcgga | tgatcttcac | actccagttg | tattggctgg | aatgtctgat | ccattaaaat | 1380 |
| caatcaatga | tttgctgcat | gctcgtaagg | ggaaaaaaca | acaatttcga | atcgaatcac | 1440 |
| tatcagcttt | ggagaagagc | gtcagggatg | tccttactgt | tttaggactt | atgcctgcaa | 1500 |
| gttactctga | ggttttgcag | cagcttaagg | taaaagcttt | aaaacgtgca | aactttacgg | 1560 |
| aagaagaagt | cttgcagaaa | attgaagaac | gggctactgc | tagaatgcaa | aaggagtatg | 1620 |
| ctaaatcgga | tgcaatcagg | aaggatttgg | ctgtacttgg | tattactctt | atggacagtc | 1680 |
| caaatggcac | aacttggagg | cctgccattc | tcttccact | tcaagagctg | ctctaagtca | 1740 |
| agagttgttc | aacatctcca | aagcaaaacc | aagaaatgta | agttactagg | ttctggtata | 1800 |
| tggaaatcaa | ttataaggga | tgccacgggt | gtatctcgct | atcaacttct | cagaatgata | 1860 |

-continued

```
aaggcgaccc cttcttaact cttgatgccg taaaaacatg gattacaatt tacgttttga    1920
tagagatgtg cttagtgtag ttgtcttggt gaccaatatt gaatttttt tttttcttca     1980 tataccgggc ttttaacccc tagagtattc atagtttcaa cgaatttgag tttcagatta   2040
atattaaaat aaatagtcgc actatcacta gagtagtgtt atgtttctac tttctagagt   2100
agcttcggtt taatattgag aaagacattt tttttgtggt gataatgaat tttctgttgt   2160
tttttaaaaa aaaaaaaaaa aaa                                           2183
```

<210> SEQ ID NO 14
<211> LENGTH: 574
<212> TYPE: PRT
<213> ORGANISM: Glycine max

<400> SEQUENCE: 14

```
Thr Ile Thr Leu Phe Gly Cys Glu Phe Gly Met Ser Trp Ser Gly Ala
 1               5                  10                  15

Lys Met Gly Thr Val Ser Leu Leu Lys Cys Tyr Arg Pro Phe Phe Ser
            20                  25                  30

Met Leu Phe Pro His Ser Ala Pro Pro Arg Leu His Ala Ala Ile Phe
        35                  40                  45

Arg Ser Lys Asn Phe Ser Phe Cys Ala Thr Ser Ser Pro Pro Leu Thr
    50                  55                  60

Ala Glu Lys Gly Cys Gly Lys Ser Asp Ala Glu Cys Pro Thr Leu Pro
65                  70                  75                  80

Glu Val Trp Leu His Asn Thr Met Ser Arg Thr Lys Glu Leu Phe Lys
                85                  90                  95

Pro Lys Val Glu Ser Lys Val Gly Met Tyr Val Cys Gly Val Thr Ala
            100                 105                 110

Tyr Asp Leu Ser His Ile Gly His Ala Arg Val Tyr Val Asn Phe Asp
        115                 120                 125

Leu Leu Tyr Arg Tyr Phe Lys His Leu Gly Phe Glu Val Cys Tyr Val
    130                 135                 140

Arg Asn Phe Thr Asp Val Asp Asp Lys Ile Ile Ala Arg Ala Lys Glu
145                 150                 155                 160

Leu Gly Glu Asp Pro Ile Ser Leu Ser Trp Arg Tyr Cys Glu Glu Phe
                165                 170                 175

Cys Gln Asp Met Val Thr Leu Asn Cys Leu Ser Pro Ser Val Glu Pro
            180                 185                 190

Lys Val Ser Glu His Met Pro Gln Ile Ile Asp Met Ile Glu Lys Ile
        195                 200                 205

Leu Asn Asn Gly Tyr Ala Tyr Ile Val Asp Gly Asp Val Tyr Phe Asn
    210                 215                 220

Val Glu Lys Phe Pro Glu Tyr Gly Lys Leu Ser Ser Arg Asp Leu Glu
225                 230                 235                 240

Asp Asn Arg Ala Gly Glu Arg Val Ala Val Asp Ser Arg Lys Lys Asn
                245                 250                 255

Pro Ala Asp Phe Ala Leu Trp Lys Ser Ala Lys Pro Gly Glu Pro Phe
            260                 265                 270

Trp Glu Ser Pro Trp Gly Pro Gly Arg Pro Gly Trp His Ile Glu Cys
        275                 280                 285

Ser Ala Met Ser Ala Ala Tyr Leu Gly Tyr Ser Phe Asp Ile His Gly
    290                 295                 300

Gly Gly Ile Asp Leu Val Phe Pro His His Glu Asn Glu Ile Ala Gln
305                 310                 315                 320
```

Ser Cys Ala Ala Cys Lys Lys Ser Asp Ile Ser Ile Trp Met His Asn
            325                 330                 335
Gly Phe Val Thr Ile Asp Ser Val Lys Met Ser Lys Ser Leu Gly Asn
            340                 345                 350
Phe Phe Thr Ile Arg Gln Val Ile Asp Val Tyr His Pro Leu Ala Leu
            355                 360                 365
Arg Tyr Phe Leu Met Ser Ala His Tyr Arg Ser Pro Ile Asn Tyr Ser
            370                 375                 380
Asn Ile Gln Leu Glu Ser Ala Ser Asp Arg Val Phe Tyr Ile Tyr Glu
385                 390                 395                 400
Thr Leu His Glu Cys Glu Ser Phe Leu Asn Gln His Asp Gln Arg Lys
            405                 410                 415
Asp Ser Thr Pro Pro Asp Thr Leu Asp Ile Ile Asp Lys Phe His Asp
            420                 425                 430
Val Phe Leu Thr Ser Met Ser Asp Asp Leu His Thr Pro Val Val Leu
            435                 440                 445
Ala Gly Met Ser Asp Pro Leu Lys Ser Ile Asn Asp Leu Leu His Ala
            450                 455                 460
Arg Lys Gly Lys Lys Gln Gln Phe Arg Ile Glu Ser Leu Ser Ala Leu
465                 470                 475                 480
Glu Lys Ser Val Arg Asp Val Leu Thr Val Leu Gly Leu Met Pro Ala
            485                 490                 495
Ser Tyr Ser Glu Val Leu Gln Gln Leu Lys Val Lys Ala Leu Lys Arg
            500                 505                 510
Ala Asn Phe Thr Glu Glu Val Leu Gln Lys Ile Glu Glu Arg Ala
            515                 520                 525
Thr Ala Arg Met Gln Lys Glu Tyr Ala Lys Ser Asp Ala Ile Arg Lys
            530                 535                 540
Asp Leu Ala Val Leu Gly Ile Thr Leu Met Asp Ser Pro Asn Gly Thr
545                 550                 555                 560
Thr Trp Arg Pro Ala Ile Pro Leu Pro Leu Gln Glu Leu Leu
            565                 570

<210> SEQ ID NO 15
<211> LENGTH: 633
<212> TYPE: DNA
<213> ORGANISM: Zea mays

<400> SEQUENCE: 15
gcacacacgt cggtccaaac acgcgccgtc cgctcgcggc ttctccaacc aaagccgtgc      60
agccaaatcc gaagggtagc gtagcacggg gacgacgcca tgagccgcgc gctcctctcc     120
cacgtcctcc accgtccgcc gcacttcgcg tacacctgct taaggagtgg cgttggtgcc     180
cgaggaggag tgctcgcttc tggcatccac ccactccgtc gtctcaattg cagcgcggtt     240
gaagccgttc ccggcccac cgaggaggcg cctgctcctc aggcaaggaa gaaaagagta     300
gtttctggtg tacagccaac aggatcggtt caccttggaa attatctagg ggcaattaag     360
aattgggttg cacttcagga ttcatatgag acattctttt tcatcgtgga tcttcatgca     420
attactttac catatgaggc gccactgctt tctaaagcaa caagaagcac tgctgcaata     480
tatcttgcat gtggcgtcga cagctccaag gcttctatct ttgtacagtc tcatgtccgt     540
gctcatgttg agttgatgtg gctattgagt tcttctactc ctattggctg gctgaataga     600
atgatccagt tcaaagagaa gtctcgcaag gcg                                  633

```
<210> SEQ ID NO 16
<211> LENGTH: 410
<212> TYPE: PRT
<213> ORGANISM: Zea mays

<400> SEQUENCE: 16

His Gly Asp Asp Ala Met Ser Arg Ala Leu Leu Ser His Val Leu His
  1               5                  10                  15

Arg Pro Pro His Phe Ala Tyr Thr Cys Leu Arg Ser Gly Val Gly Ala
             20                  25                  30

Arg Gly Gly Val Leu Ala Ser Gly Ile His Pro Leu Arg Arg Leu Asn
         35                  40                  45

Cys Ser Ala Val Glu Ala Val Pro Gly Pro Thr Glu Glu Ala Pro Ala
     50                  55                  60

Pro Gln Ala Arg Lys Lys Arg Val Val Ser Gly Val Gln Pro Thr Gly
 65                  70                  75                  80

Ser Val His Leu Gly Asn Tyr Leu Gly Ala Ile Lys Asn Trp Val Ala
                 85                  90                  95

Leu Gln Asp Ser Tyr Glu Thr Phe Phe Ile Val Asp Leu His Ala
            100                 105                 110

Ile Thr Leu Pro Tyr Glu Ala Pro Leu Leu Ser Lys Ala Thr Arg Ser
        115                 120                 125

Thr Ala Ala Ile Tyr Leu Ala Cys Gly Val Asp Ser Ser Lys Ala Ser
    130                 135                 140

Ile Phe Val Gln Ser His Val Arg Ala His Val Glu Leu Met Trp Leu
145                 150                 155                 160

Leu Ser Ser Ser Thr Pro Ile Gly Trp Leu Asn Arg Met Ile Gln Phe
                165                 170                 175

Lys Glu Lys Ser Arg Lys Ala Gly Asp Glu Asn Val Gly Val Ala Leu
            180                 185                 190

Leu Thr Tyr Pro Val Leu Met Ala Ser Asp Ile Leu Leu Tyr Gln Ser
        195                 200                 205

Asp Leu Val Pro Val Gly Glu Asp Gln Thr Gln His Leu Glu Leu Thr
    210                 215                 220

Arg Glu Ile Ala Glu Arg Val Asn Asn Leu Tyr Gly Gly Arg Lys Trp
225                 230                 235                 240

Lys Lys Leu Gly Gly Arg Gly Leu Leu Phe Lys Val Pro Glu Ala
                245                 250                 255

Leu Ile Pro Pro Ala Gly Ala Arg Val Met Ser Leu Thr Asp Gly Leu
            260                 265                 270

Ser Lys Met Ser Lys Ser Ala Pro Ser Asp Gln Ser Arg Ile Asn Leu
        275                 280                 285

Leu Asp Pro Lys Asp Val Ile Ala Asn Lys Ile Lys Arg Cys Lys Thr
    290                 295                 300

Asp Ser Phe Pro Gly Met Glu Phe Asp Asn Pro Glu Arg Pro Glu Cys
305                 310                 315                 320

Arg Asn Leu Leu Ser Ile Tyr Gln Ile Ile Thr Glu Lys Thr Lys Glu
                325                 330                 335

Glu Val Val Ser Glu Cys Gln His Met Asn Trp Gly Thr Phe Lys Thr
            340                 345                 350

Thr Leu Thr Glu Ala Leu Ile Asp His Leu Gln Pro Ile Gln Val Arg
        355                 360                 365

Tyr Glu Glu Ile Met Ser Asp Pro Ala Tyr Leu Asp Asn Val Leu Leu
    370                 375                 380
```

Glu Gly Ala Val Lys Ala Ala Glu Ile Ala Asp Ile Thr Leu Asn Asn
385                 390                 395                 400

Val Tyr Gln Ala Met Gly Phe Leu Arg Arg
            405                 410

<210> SEQ ID NO 17
<211> LENGTH: 1536
<212> TYPE: DNA
<213> ORGANISM: Glycine max

<400> SEQUENCE: 17

| gcacgaggga | agatgagcgt | ttcacatttc | gcggttctat | cgtcgtgttg | ttgtccacgc | 60 |
| ttggccccctt | ctctgtcgcg | tgcttcaacc | cttcgttctc | gcatccggtg | ttgtactact | 120 |
| ctcactgcta | cttcttcaga | gactcccact | ccaaccttcg | tgaagaaacg | agtagtgtcg | 180 |
| ggggttcagc | ccacgggctc | aattcacctc | ggaaactatt | tggcgccat | caagaattgg | 240 |
| gttgccccttc | agaatgtgta | tgatacactt | ttcttcattg | tggacctgca | cgcgattaca | 300 |
| ttaccatatg | acacccaaca | attatctaag | gctacaaggt | caactgctgc | tatttaccta | 360 |
| gcatgtggag | tggatccttc | aaaggcttca | gtatttgtac | agtctcatgt | tcgggcacat | 420 |
| gtagaattga | tgtggctgct | aagttccaca | acaccaattg | gttggctgaa | caaaatgata | 480 |
| caatttaaag | agaaatctcg | caaggcggga | gatgaagaag | ttggggttgc | ccttttgact | 540 |
| tatcctgttc | tgatggcttc | tgatatactt | ctatatcagt | ctgattttgt | ccctgttggt | 600 |
| gaagatcaaa | agcagcactt | ggagttgact | cgtgacttgg | ctgaacgggt | taataattta | 660 |
| tatggaggaa | gaaagtggaa | gaaattaggc | ggttatgaca | gccgaggtgg | tactatattt | 720 |
| aaggttccag | agcccttat | acctccagcc | ggagcccgga | taatgtccct | aactgatggc | 780 |
| ctgtccaaga | tgtcaaagtc | tgcaccttct | gatcaatcca | gaatcaatat | tcttgatcct | 840 |
| aaagatctca | tagcaaacaa | gatcaaacgt | tgcaaaactg | attcatttcc | tggcttggaa | 900 |
| tttgacaact | ctgagaggcc | tgaatgtaac | aatcttgttt | ccatatacca | gcttatttca | 960 |
| ggaaagacga | agaggaagt | tgtgcaggaa | tgccaaaaca | tgaactgggg | cacattcaaa | 1020 |
| cctcttttaa | cagatgcctt | gattgatcat | ttgcatccca | ttcaggttcg | ctatgaggaa | 1080 |
| atcatgtccg | attcaggtta | tttagatgga | gttttagcac | aaggtgctag | aaatgcagca | 1140 |
| gatatagcag | attctacact | taataatatt | taccaagcaa | tgggattttt | taagagacag | 1200 |
| tgataattga | tgccaaataa | attaaagatt | ggcgagacgt | caacttaaaa | gctaacttct | 1260 |
| ggatgattca | tgatgggcct | caaaattttg | gagtaatctt | atggacatat | acttgactac | 1320 |
| tggaaatgga | aagattattg | atgcaaagcc | taaaggtccc | attagttctt | gatgcaatgg | 1380 |
| gctttgtatc | tccttcattt | ttctccgagt | atggtcgttg | ccttcatttt | atattttatt | 1440 |
| gtttcaatct | ctttcattat | ttacttgtat | tttataatga | attcagcata | ttgataaatt | 1500 |
| gttccgccat | tgtatttaaa | aaaaaaaaaa | aaaaaa |  |  | 1536 |

<210> SEQ ID NO 18
<211> LENGTH: 400
<212> TYPE: PRT
<213> ORGANISM: Glycine max

<400> SEQUENCE: 18

Ala Arg Gly Lys Met Ser Val Ser His Phe Ala Val Leu Ser Ser Cys
 1               5                  10                  15

Cys Cys Pro Arg Leu Ala Pro Ser Leu Ser Arg Ala Ser Thr Leu Arg

|   | 20 |   |   | 25 |   |   | 30 |   |
|---|---|---|---|---|---|---|---|---|

Ser Arg Ile Arg Cys Cys Thr Thr Leu Thr Ala Thr Ser Ser Glu Thr
                 35                  40                  45

Pro Thr Pro Thr Phe Val Lys Lys Arg Val Val Ser Gly Val Gln Pro
 50                  55                  60

Thr Gly Ser Ile His Leu Gly Asn Tyr Phe Gly Ala Ile Lys Asn Trp
 65                  70                  75                  80

Val Ala Leu Gln Asn Val Tyr Asp Thr Leu Phe Phe Ile Val Asp Leu
                 85                  90                  95

His Ala Ile Thr Leu Pro Tyr Asp Thr Gln Gln Leu Ser Lys Ala Thr
                100                 105                 110

Arg Ser Thr Ala Ala Ile Tyr Leu Ala Cys Gly Val Asp Pro Ser Lys
                115                 120                 125

Ala Ser Val Phe Val Gln Ser His Val Arg Ala His Val Glu Leu Met
130                 135                 140

Trp Leu Leu Ser Ser Thr Thr Pro Ile Gly Trp Leu Asn Lys Met Ile
145                 150                 155                 160

Gln Phe Lys Glu Lys Ser Arg Lys Ala Gly Asp Glu Glu Val Gly Val
                165                 170                 175

Ala Leu Leu Thr Tyr Pro Val Leu Met Ala Ser Asp Ile Leu Leu Tyr
                180                 185                 190

Gln Ser Asp Phe Val Pro Val Gly Glu Asp Gln Lys Gln His Leu Glu
                195                 200                 205

Leu Thr Arg Asp Leu Ala Glu Arg Val Asn Asn Leu Tyr Gly Gly Arg
                210                 215                 220

Lys Trp Lys Lys Leu Gly Gly Tyr Asp Ser Arg Gly Gly Thr Ile Phe
225                 230                 235                 240

Lys Val Pro Glu Pro Leu Ile Pro Pro Ala Gly Ala Arg Ile Met Ser
                245                 250                 255

Leu Thr Asp Gly Leu Ser Lys Met Ser Lys Ser Ala Pro Ser Asp Gln
                260                 265                 270

Ser Arg Ile Asn Ile Leu Asp Pro Lys Asp Leu Ile Ala Asn Lys Ile
                275                 280                 285

Lys Arg Cys Lys Thr Asp Ser Phe Pro Gly Leu Glu Phe Asp Asn Ser
290                 295                 300

Glu Arg Pro Glu Cys Asn Asn Leu Val Ser Ile Tyr Gln Leu Ile Ser
305                 310                 315                 320

Gly Lys Thr Lys Glu Glu Val Val Gln Glu Cys Gln Asn Met Asn Trp
                325                 330                 335

Gly Thr Phe Lys Pro Leu Leu Thr Asp Ala Leu Ile Asp His Leu His
                340                 345                 350

Pro Ile Gln Val Arg Tyr Glu Glu Ile Met Ser Asp Ser Gly Tyr Leu
                355                 360                 365

Asp Gly Val Leu Ala Gln Gly Ala Arg Asn Ala Ala Asp Ile Ala Asp
370                 375                 380

Ser Thr Leu Asn Asn Ile Tyr Gln Ala Met Gly Phe Phe Lys Arg Gln
385                 390                 395                 400

<210> SEQ ID NO 19
<211> LENGTH: 725
<212> TYPE: DNA
<213> ORGANISM: Triticum aestivum

<400> SEQUENCE: 19

```
ctcgtgccga attcggcacg aggcggttca ttatttaagg ttcctgaagc ccttatccct      60
ccagcagggg cccgtgtgat gtccttaact gatggcctct ccaagatgtc gaagtctgct     120
ccttcagatt tgtctcgcat taaccttctt gacccaaatg atgtgattgt gaacaaaatc     180
aaacgctgca aaactgactc gctccctggc ttggaattcg acaacccaga gaggccggaa     240
tgcaaaaatc ttctctcagt ctaccagatc atcactggaa aaacgaaaga ggaagttgtt     300
agtgaatgcc aagatatgaa ctgggggacg ttcaaggtta cccttacgga tgccttaatt     360
gatcatctgc aacctattca ggttcgatac gaggagatca tgtctgatcc aggttatttg     420
gacaatgttc tgctaaatgg ggcagggaaa gcttctgaga tagcagacgc caccctcaac     480
aacgtctacc aagccatggg tttcttgcgc agatagcata tgtagaacat tttttataac     540
tgcacaatgc tagttttgca cttgttggcc tttctgctag tggtactgat aagcgttttg     600
tttgatatgc ttggattagc cttttgttcc tggttattat ggacactgtt aataggtatt     660
aaaaggatta tttactgaaa aaaaaaaaaa aaaaaaaaa  attaaaaggg ggcgcgcgta     720
ccata                                                                725

<210> SEQ ID NO 20
<211> LENGTH: 171
<212> TYPE: PRT
<213> ORGANISM: Triticum aestivum

<400> SEQUENCE: 20

Leu Val Pro Asn Ser Ala Arg Gly Gly Ser Leu Phe Lys Val Pro Glu
  1               5                  10                  15

Ala Leu Ile Pro Pro Ala Gly Ala Arg Val Met Ser Leu Thr Asp Gly
                 20                  25                  30

Leu Ser Lys Met Ser Lys Ser Ala Pro Ser Asp Leu Ser Arg Ile Asn
             35                  40                  45

Leu Leu Asp Pro Asn Asp Val Ile Val Asn Lys Ile Lys Arg Cys Lys
         50                  55                  60

Thr Asp Ser Leu Pro Gly Leu Glu Phe Asp Asn Pro Glu Arg Pro Glu
 65                  70                  75                  80

Cys Lys Asn Leu Leu Ser Val Tyr Gln Ile Ile Thr Gly Lys Thr Lys
                 85                  90                  95

Glu Glu Val Val Ser Glu Cys Gln Asp Met Asn Trp Gly Thr Phe Lys
            100                 105                 110

Val Thr Leu Thr Asp Ala Leu Ile Asp His Leu Gln Pro Ile Gln Val
            115                 120                 125

Arg Tyr Glu Glu Ile Met Ser Asp Pro Gly Tyr Leu Asp Asn Val Leu
        130                 135                 140

Leu Asn Gly Ala Gly Lys Ala Ser Glu Ile Ala Asp Ala Thr Leu Asn
145                 150                 155                 160

Asn Val Tyr Gln Ala Met Gly Phe Leu Arg Arg
                165                 170

<210> SEQ ID NO 21
<211> LENGTH: 1062
<212> TYPE: DNA
<213> ORGANISM: Zea mays

<400> SEQUENCE: 21
gcacgaggga catcacgctg ctggatttcc tgagagaggt gggccgtttt gcacgcgtgg      60
gtacaatgat cgccaaggag agcgtcaaga agcgtcttgc gtcggaagac gggatgagct     120
```

-continued

| | |
|---|---|
| acaccgagtt tacctaccag ctgctgcagg gctacgactt cctttacatg ttcaagaata | 180 |
| tgggtgtcaa tgtgcagatc gggggcagcg atcagtgggg aacatcaca gcgggaactg | 240 |
| agttgatcag aaaaatcttg caggttgaag gggcgcatgg actcacattc ccacttctgc | 300 |
| tgaagagcga cggtaccaaa tttggaaaga cggaggatgg ggcaatctgg ctctcttcga | 360 |
| agatgctttc tccttacaag ttctatcagt acttctttgc ggtgccagac atcgatgtca | 420 |
| tcaggtttat gaagatcctg acgttcctga gcttggatga gattctggag ctagaagact | 480 |
| cgatgaagaa gcctggctat gtgccaaaca ctgttcagaa gaggcttgca aagaggtga | 540 |
| cgcgatttgt tcatggcgag gagggattgg aggaggcatt gaaggcaacc gaggccttga | 600 |
| gacctggtgc tcagacacaa ttggatgcac aaacaattga ggggatagca gatgatgtgc | 660 |
| cttcatgctc tttagcttat gatcaagtgt tcaagtctcc acttattgat ttggctgttt | 720 |
| ccacaggttt gctcactagt aagtcagcag ttaagcggct tattaagcaa ggtggtctgt | 780 |
| acttgaataa cgtgaggatt gatagtgagg ataagctggt tgaggaaggt gatatagttg | 840 |
| atgggaaggt gctcttgttg tctgctggaa agaagaacaa gatggttgtg aggatatctt | 900 |
| gactactctt atttgttctt tataacttat tttagccatt gaggagaaaa gtaacggtgt | 960 |
| tgtgtcttca aaactcaaat gagctgtcta tgagcataca gattgttata ttggagaggt | 1020 |
| tgaacacacc ttttttttg ctctaaaaaa aaaaaaaaaa aa | 1062 |

<210> SEQ ID NO 22
<211> LENGTH: 299
<212> TYPE: PRT
<213> ORGANISM: Zea mays

<400> SEQUENCE: 22

Thr Arg Asp Ile Thr Leu Leu Asp Phe Leu Arg Glu Val Gly Arg Phe
 1               5                  10                  15

Ala Arg Val Gly Thr Met Ile Ala Lys Glu Ser Val Lys Lys Arg Leu
            20                  25                  30

Ala Ser Glu Asp Gly Met Ser Tyr Thr Glu Phe Thr Tyr Gln Leu Leu
        35                  40                  45

Gln Gly Tyr Asp Phe Leu Tyr Met Phe Lys Asn Met Gly Val Asn Val
    50                  55                  60

Gln Ile Gly Gly Ser Asp Gln Trp Gly Asn Ile Thr Ala Gly Thr Glu
65                  70                  75                  80

Leu Ile Arg Lys Ile Leu Gln Val Glu Gly Ala His Gly Leu Thr Phe
                85                  90                  95

Pro Leu Leu Lys Ser Asp Gly Thr Lys Phe Gly Lys Thr Glu Asp
            100                 105                 110

Gly Ala Ile Trp Leu Ser Ser Lys Met Leu Ser Pro Tyr Lys Phe Tyr
        115                 120                 125

Gln Tyr Phe Ala Val Pro Asp Ile Asp Val Ile Arg Phe Met Lys
    130                 135                 140

Ile Leu Thr Phe Leu Ser Leu Asp Glu Ile Leu Glu Leu Glu Asp Ser
145                 150                 155                 160

Met Lys Lys Pro Gly Tyr Val Pro Asn Thr Val Gln Lys Arg Leu Ala
                165                 170                 175

Glu Glu Val Thr Arg Phe Val His Gly Glu Gly Leu Glu Glu Ala
            180                 185                 190

Leu Lys Ala Thr Glu Ala Leu Arg Pro Gly Ala Gln Thr Gln Leu Asp
        195                 200                 205

```
Ala Gln Thr Ile Glu Gly Ile Ala Asp Asp Val Pro Ser Cys Ser Leu
    210                 215                 220
Ala Tyr Asp Gln Val Phe Lys Ser Pro Leu Ile Asp Leu Ala Val Ser
225                 230                 235                 240
Thr Gly Leu Leu Thr Ser Lys Ser Ala Val Lys Arg Leu Ile Lys Gln
                245                 250                 255
Gly Gly Leu Tyr Leu Asn Asn Val Arg Ile Asp Ser Glu Asp Lys Leu
            260                 265                 270
Val Glu Glu Gly Asp Ile Val Asp Gly Lys Val Leu Leu Leu Ser Ala
        275                 280                 285
Gly Lys Lys Asn Lys Met Val Val Arg Ile Ser
290                 295
```

<210> SEQ ID NO 23
<211> LENGTH: 346
<212> TYPE: PRT
<213> ORGANISM: Drosophila melanogaster

<400> SEQUENCE: 23

```
Met Val Asp Lys Val Ala Asn Gly Val Ser Lys Gly Ala Lys Lys
  1               5                  10                  15
Ala Lys Ala Ala Lys Lys Ala Lys Ala Asn Ala Ser Thr Ala Ala Ala
             20                  25                  30
Asn Asn Ser Gly Gly Asp Ser Ala Asp His Ala Ala Gly Arg Tyr Gly
            35                  40                  45
Ser Met Ser Lys Asp Lys Arg Ser Arg Asn Val Val Ser Ser Gly Val
        50                  55                  60
Gly Lys Gly Val Trp Val Arg Gly Arg Val His Thr Ser Arg Ala Lys
65                  70                  75                  80
Gly Lys Cys Arg Ser Ser Thr Val Cys Ala Val Gly Asp Val Ser Lys
                85                  90                  95
Met Val Lys Ala Gly Asn Lys Ser Asp Ala Lys Val Ala Val Ser Ser
            100                 105                 110
Lys Ser Cys Thr Ser Ser Val Val Ser Ala Lys Ala Asp Ala Ser Arg
        115                 120                 125
Asn Ala Asp Asp Ala Gly Asn Arg Val Asn Asp Thr Arg Asp Asn Arg
130                 135                 140
Val Asp Arg Thr Ala Asn Ala Arg Ala Gly Val Cys Arg Arg Asp Thr
145                 150                 155                 160
Gly Thr His Thr Lys Ser Ala Ala Ser Gly Gly Ala Asn Val Thr Val
                165                 170                 175
Ser Tyr Lys Asp Ser Ala Tyr Ala Ser Tyr Lys Met Ala Ala Ala Asp
            180                 185                 190
Asp Lys Val Tyr Thr Val Gly Ala Val Arg Ala Asp Ser Asn Thr His
        195                 200                 205
Arg His Thr Val Gly Asp Met Ala Lys Tyr His Tyr His Val His Thr
210                 215                 220
Gly Asn Thr Thr Ser Lys Gly Arg Asp Lys Tyr Ala Lys Ser Val Gly
225                 230                 235                 240
Tyr Lys Val Asp Ala Lys Ala Asp Gly Val Ala Met Arg Ala Gly Val
                245                 250                 255
Thr Gly Asp Asp Ser Thr Asn Lys Gly Arg Val Lys Ala Lys Tyr Asp
            260                 265                 270
Thr Asp Tyr Asp Lys Ala Arg Tyr Thr Met Asp Asn Asn Val Tyr Ser
        275                 280                 285
```

```
Asn Ser Tyr Asp Met Met Arg Gly Ser Gly Ala Arg His Asp Tyr Arg
    290                 295                 300

Ala Lys His His Gly Asp Thr Ser Lys Ala Ala Tyr Ser Arg Tyr Gly
305                 310                 315                 320

Cys His Ala Gly Gly Gly Met Arg Val Val Met Tyr Gly Asp Asn
                325                 330                 335

Arg Lys Thr Ser Met Arg Asp Lys Arg Thr
            340                 345

<210> SEQ ID NO 24
<211> LENGTH: 501
<212> TYPE: PRT
<213> ORGANISM: Rattus norvegicus

<400> SEQUENCE: 24

Met Pro Ser Ala Asn Ala Ser Arg Lys Gly Gln Glu Lys Pro Arg Glu
 1               5                  10                  15

Ile Val Asp Ala Ala Glu Asp Tyr Ala Lys Glu Arg Tyr Gly Val Ser
            20                  25                  30

Ser Met Ile Gln Ser Gln Glu Lys Pro Asp Arg Val Leu Val Arg Val
         35                  40                  45

Lys Asp Leu Thr Val Gln Lys Ala Asp Glu Val Val Trp Val Arg Ala
 50                  55                  60

Arg Val His Thr Ser Arg Ala Lys Gly Lys Gln Cys Phe Leu Val Leu
 65                  70                  75                  80

Arg Gln Gln Gln Phe Asn Val Gln Ala Leu Val Ala Val Gly Asp His
                 85                  90                  95

Ala Ser Lys Gln Met Val Lys Phe Ala Ala Asn Ile Asn Lys Glu Ser
            100                 105                 110

Ile Ile Asp Val Glu Gly Ile Val Arg Lys Val Asn Gln Lys Ile Gly
         115                 120                 125

Ser Cys Thr Gln Gln Asp Val Glu Leu His Val Gln Lys Ile Tyr Val
130                 135                 140

Ile Ser Leu Ala Glu Pro Arg Leu Pro Leu Gln Leu Asp Asp Ala Ile
145                 150                 155                 160

Arg Pro Glu Val Glu Gly Glu Asp Gly Arg Ala Thr Val Asn Gln
                165                 170                 175

Asp Thr Arg Leu Asp Asn Arg Ile Ile Asp Leu Arg Thr Ser Thr Ser
            180                 185                 190

Gln Ala Ile Phe His Leu Gln Ser Gly Ile Cys His Leu Phe Arg Glu
        195                 200                 205

Thr Leu Ile Asn Lys Gly Phe Val Glu Ile Gln Thr Pro Lys Ile Ile
210                 215                 220

Ser Ala Ala Ser Glu Gly Gly Ala Asn Val Phe Thr Val Ser Tyr Phe
225                 230                 235                 240

Lys Ser Asn Ala Tyr Leu Ala Gln Ser Pro Gln Leu Tyr Lys Gln Met
                245                 250                 255

Cys Ile Cys Ala Asp Phe Glu Lys Val Phe Cys Ile Gly Pro Val Phe
            260                 265                 270

Arg Ala Glu Asp Ser Asn Thr His Arg His Leu Thr Glu Phe Val Gly
        275                 280                 285

Leu Asp Ile Glu Met Ala Phe Asn Tyr His Tyr His Glu Val Val Glu
290                 295                 300

Glu Ile Ala Asp Thr Leu Val Gln Ile Phe Lys Gly Leu Gln Glu Arg
```

-continued

```
                305                 310                 315                 320
Phe Gln Thr Glu Ile Gln Thr Val Asn Lys Gln Phe Pro Cys Glu Pro
                    325                 330                 335
Phe Lys Phe Leu Glu Pro Thr Leu Arg Leu Glu Tyr Cys Glu Ala Leu
                340                 345                 350
Ala Met Leu Arg Glu Ala Gly Val Glu Met Asp Asp Glu Glu Asp Leu
                355                 360                 365
Ser Thr Pro Asn Glu Lys Leu Leu Gly Arg Leu Val Lys Glu Lys Tyr
            370                 375                 380
Asp Thr Asp Phe Tyr Val Leu Asp Lys Tyr Pro Leu Ala Val Arg Pro
385                 390                 395                 400
Phe Tyr Thr Met Pro Asp Pro Arg Asn Pro Lys Gln Ser Asn Ser Tyr
                    405                 410                 415
Asp Met Phe Met Arg Gly Glu Glu Ile Leu Ser Gly Ala Gln Arg Ile
                420                 425                 430
His Asp Pro Gln Leu Leu Thr Glu Arg Ala Leu His His Gly Ile Asp
            435                 440                 445
Leu Glu Lys Ile Lys Ala Tyr Ile Asp Ser Phe Arg Phe Gly Ala Pro
450                 455                 460
Pro His Ala Gly Gly Gly Ile Gly Leu Glu Arg Val Thr Met Leu Phe
465                 470                 475                 480
Leu Gly Leu His Asn Val Arg Gln Thr Ser Met Phe Pro Arg Asp Pro
                    485                 490                 495
Lys Arg Leu Thr Pro
                500

<210> SEQ ID NO 25
<211> LENGTH: 500
<212> TYPE: PRT
<213> ORGANISM: Homo sapiens

<400> SEQUENCE: 25

Met Pro Ser Ala Thr Gln Arg Lys Ser Gln Glu Lys Pro Arg Glu Ile
1               5                   10                  15
Met Asp Ala Ala Glu Asp Tyr Ala Lys Glu Arg Tyr Gly Ile Ser Ser
                20                  25                  30
Met Ile Gln Ser Gln Glu Lys Pro Asp Arg Val Leu Val Arg Val Arg
            35                  40                  45
Asp Leu Thr Ile Gln Lys Ala Asp Glu Val Val Trp Val Arg Ala Arg
        50                  55                  60
Val His Thr Ser Arg Ala Lys Gly Lys Gln Cys Phe Leu Val Leu Arg
65                  70                  75                  80
Gln Gln Gln Phe Asn Val Gln Ala Leu Val Ala Val Gly Asp His Ala
                85                  90                  95
Ser Lys Gln Met Val Lys Phe Ala Ala Asn Ile Asn Lys Glu Ser Ile
                100                 105                 110
Val Asp Val Glu Gly Val Val Arg Lys Val Asn Gln Lys Ile Gly Ser
            115                 120                 125
Cys Thr Gln Gln Asp Val Glu Leu His Val Gln Lys Ile Tyr Val Ile
        130                 135                 140
Ser Leu Ala Glu Pro Arg Leu Pro Leu Gln Leu Asp Asp Ala Val Arg
145                 150                 155                 160
Pro Glu Gln Glu Gly Glu Glu Gly Arg Ala Thr Val Asn Gln Asp
                165                 170                 175
```

```
Thr Arg Leu Asp Asn Arg Val Ile Asp Leu Arg Thr Ser Thr Ser Gln
            180                 185                 190

Ala Val Phe Arg Leu Gln Ser Gly Ile Cys His Leu Phe Arg Glu Thr
        195                 200                 205

Leu Ile Asn Lys Gly Phe Val Glu Ile Gln Thr Pro Lys Ile Ile Ser
    210                 215                 220

Ala Ala Ser Glu Gly Gly Ala Asn Val Phe Thr Val Ser Tyr Phe Lys
225                 230                 235                 240

Asn Asn Ala Tyr Leu Ala Gln Ser Pro Gln Leu Tyr Lys Gln Met Cys
                245                 250                 255

Ile Cys Ala Asp Phe Glu Lys Val Phe Ser Ile Gly Pro Val Phe Arg
            260                 265                 270

Ala Glu Asp Ser Asn Thr His Arg His Leu Thr Glu Phe Val Gly Leu
        275                 280                 285

Asp Ile Glu Met Ala Phe Asn Tyr His Tyr His Glu Val Met Glu Glu
    290                 295                 300

Ile Ala Asp Thr Met Val Gln Ile Phe Lys Gly Leu Gln Glu Arg Phe
305                 310                 315                 320

Gln Thr Glu Ile Gln Thr Val Asn Lys Gln Phe Pro Cys Glu Pro Phe
                325                 330                 335

Lys Phe Leu Glu Pro Thr Leu Arg Leu Glu Tyr Cys Glu Ala Leu Ala
            340                 345                 350

Met Leu Arg Glu Ala Gly Val Glu Met Gly Asp Glu Asp Leu Ser
        355                 360                 365

Thr Pro Asn Glu Lys Leu Leu Gly His Leu Val Lys Glu Lys Tyr Asp
    370                 375                 380

Thr Asp Phe Tyr Ile Leu Asp Lys Tyr Pro Leu Ala Val Arg Pro Phe
385                 390                 395                 400

Tyr Thr Met Pro Asp Pro Arg Asn Pro Lys Gln Ser Lys Ser Tyr Asp
                405                 410                 415

Met Phe Met Arg Gly Glu Glu Ile Leu Ser Gly Ala Gln Arg Ile His
            420                 425                 430

Asp Pro Gln Leu Leu Thr Glu Arg Ala Leu His His Gly Asn Asp Leu
        435                 440                 445

Glu Lys Ile Lys Ala Tyr Ile Asp Ser Phe Arg Phe Gly Ala Pro Pro
    450                 455                 460

His Ala Gly Gly Gly Ile Gly Leu Glu Arg Val Thr Met Leu Phe Leu
465                 470                 475                 480

Gly Leu His Asn Val Arg Gln Thr Ser Met Phe Pro Arg Asp Pro Lys
                485                 490                 495

Arg Leu Thr Pro
            500

<210> SEQ ID NO 26
<211> LENGTH: 459
<212> TYPE: PRT
<213> ORGANISM: Haemophilus influenzae Rd

<400> SEQUENCE: 26

Met Leu Lys Ile Phe Asn Thr Leu Thr Arg Glu Lys Glu Ile Phe Lys
  1               5                  10                  15

Pro Ile His Glu Asn Lys Val Gly Met Tyr Val Cys Gly Val Thr Val
                20                  25                  30

Tyr Asp Leu Cys His Ile Gly His Gly Arg Thr Phe Val Cys Phe Asp
            35                  40                  45
```

```
Val Ile Ala Arg Tyr Leu Arg Ser Leu Gly Tyr Asp Leu Thr Tyr Val
     50                  55                  60

Arg Asn Ile Thr Asp Val Asp Lys Ile Ile Lys Arg Ala Leu Glu
 65                  70                  75                  80

Asn Lys Glu Thr Cys Asp Gln Leu Val Asp Arg Met Val Gln Glu Met
                 85                  90                  95

Tyr Lys Asp Phe Asp Ala Leu Asn Val Leu Arg Pro Asp Phe Glu Pro
                100                 105                 110

Arg Ala Thr His His Ile Pro Glu Ile Glu Ile Val Glu Lys Leu
                115                 120                 125

Ile Lys Arg Gly His Ala Tyr Val Ala Asp Asn Gly Asp Val Met Phe
130                 135                 140

Asp Val Glu Ser Phe Lys Glu Tyr Gly Lys Leu Ser Arg Gln Asp Leu
145                 150                 155                 160

Glu Gln Leu Gln Ala Gly Ala Arg Ile Glu Ile Asn Glu Ile Lys Lys
                165                 170                 175

Asn Pro Met Asp Phe Val Leu Trp Lys Met Ser Lys Glu Asn Glu Pro
                180                 185                 190

Ser Trp Ala Ser Pro Trp Gly Ala Gly Arg Pro Gly Trp His Ile Glu
                195                 200                 205

Cys Ser Ala Met Asn Cys Lys Gln Leu Gly Glu Tyr Phe Asp Ile His
                210                 215                 220

Gly Gly Gly Ser Asp Leu Met Phe Pro His His Glu Asn Glu Ile Ala
225                 230                 235                 240

Gln Ser Cys Cys Ala His Gly Gly Gln Tyr Val Asn Tyr Trp Ile His
                245                 250                 255

Ser Gly Met Ile Met Val Asp Lys Glu Lys Met Ser Lys Ser Leu Gly
                260                 265                 270

Asn Phe Phe Thr Ile Arg Asp Val Leu Asn His Tyr Asn Ala Glu Ala
                275                 280                 285

Val Arg Tyr Phe Leu Leu Thr Ala His Tyr Arg Ser Gln Leu Asn Tyr
290                 295                 300

Ser Glu Glu Asn Leu Asn Leu Ala Gln Gly Ala Leu Glu Arg Leu Tyr
305                 310                 315                 320

Thr Ala Leu Arg Gly Thr Asp Gln Ser Ala Val Ala Phe Gly Gly Glu
                325                 330                 335

Asn Phe Val Ala Thr Phe Arg Glu Ala Met Asp Asp Phe Asn Thr
                340                 345                 350

Pro Asn Ala Leu Ser Val Leu Phe Glu Met Ala Arg Glu Ile Asn Lys
                355                 360                 365

Leu Lys Thr Glu Asp Val Glu Lys Ala Asn Gly Leu Ala Ala Arg Leu
370                 375                 380

Arg Glu Leu Gly Ala Ile Leu Gly Leu Leu Gln Gln Glu Pro Glu Lys
385                 390                 395                 400

Phe Leu Gln Ala Gly Ser Asn Asp Asp Glu Val Ala Lys Ile Glu Ala
                405                 410                 415

Leu Ile Lys Gln Arg Asn Glu Ala Arg Thr Ala Lys Asp Trp Ser Ala
                420                 425                 430

Ala Asp Ser Ala Arg Asn Glu Leu Thr Ala Met Gly Ile Val Leu Glu
                435                 440                 445

Asp Gly Pro Asn Gly Thr Thr Trp Arg Lys Gln
450                 455
```

<210> SEQ ID NO 27
<211> LENGTH: 461
<212> TYPE: PRT
<213> ORGANISM: Escherichia coli

<400> SEQUENCE: 27

```
Met Leu Lys Ile Phe Asn Thr Leu Thr Arg Gln Lys Glu Phe Lys
 1               5                  10                  15

Pro Ile His Ala Gly Glu Val Gly Met Tyr Val Cys Gly Ile Thr Val
                 20                  25                  30

Tyr Asp Leu Cys His Ile Gly His Gly Arg Thr Phe Val Ala Phe Asp
                 35                  40                  45

Val Val Ala Arg Tyr Leu Arg Phe Leu Gly Tyr Lys Leu Lys Tyr Val
         50                  55                  60

Arg Asn Ile Thr Asp Ile Asp Asp Lys Ile Ile Lys Arg Ala Asn Glu
 65                  70                  75                  80

Asn Gly Glu Ser Phe Val Ala Met Val Asp Arg Met Ile Ala Glu Met
                 85                  90                  95

His Lys Asp Phe Asp Ala Leu Asn Ile Leu Arg Pro Asp Met Glu Pro
                100                 105                 110

Arg Ala Thr His His Ile Ala Glu Ile Ile Glu Leu Thr Glu Gln Leu
                115                 120                 125

Ile Ala Lys Gly His Ala Tyr Val Ala Asp Asn Gly Asp Val Met Phe
        130                 135                 140

Asp Val Pro Thr Asp Pro Thr Tyr Gly Val Leu Ser Arg Gln Asp Leu
145                 150                 155                 160

Asp Gln Leu Gln Ala Gly Ala Arg Val Asp Val Val Asp Asp Lys Arg
                165                 170                 175

Asn Pro Met Asp Phe Val Leu Trp Lys Met Ser Lys Glu Gly Glu Pro
                180                 185                 190

Ser Trp Pro Ser Pro Trp Gly Ala Gly Arg Pro Gly Trp His Ile Glu
        195                 200                 205

Cys Ser Ala Met Asn Cys Lys Gln Leu Gly Asn His Phe Asp Ile His
        210                 215                 220

Gly Gly Gly Ser Asp Leu Met Phe Pro His His Glu Asn Glu Ile Ala
225                 230                 235                 240

Gln Ser Thr Cys Ala His Asp Gly Gln Tyr Val Asn Tyr Trp Met His
                245                 250                 255

Ser Gly Met Val Met Val Asp Arg Glu Lys Met Ser Lys Ser Leu Gly
                260                 265                 270

Asn Phe Phe Thr Val Arg Asp Val Leu Lys Tyr Tyr Asp Ala Glu Thr
        275                 280                 285

Val Arg Tyr Phe Leu Met Ser Gly His Tyr Arg Ser Gln Leu Asn Tyr
    290                 295                 300

Ser Glu Glu Asn Leu Lys Gln Ala Arg Ala Ala Val Glu Arg Leu Tyr
305                 310                 315                 320

Thr Ala Leu Arg Gly Thr Asp Lys Thr Val Ala Pro Ala Gly Gly Glu
                325                 330                 335

Ala Phe Glu Ala Arg Phe Ile Glu Ala Met Asp Asp Phe Asn Thr
                340                 345                 350

Pro Glu Ala Tyr Ser Val Leu Phe Asp Met Ala Arg Glu Val Asn Arg
        355                 360                 365

Leu Lys Ala Glu Asp Met Ala Ala Ala Asn Ala Met Ala Ser His Leu
    370                 375                 380
```

-continued

```
Arg Lys Leu Ser Ala Val Leu Gly Leu Leu Glu Gln Glu Pro Glu Ala
385                 390                 395                 400

Phe Leu Gln Ser Gly Ala Gln Ala Asp Asp Ser Glu Val Ala Glu Ile
            405                 410                 415

Glu Ala Leu Ile Gln Gln Arg Leu Asp Ala Arg Lys Ala Lys Asp Trp
            420                 425                 430

Ala Ala Ala Asp Ala Ala Arg Asp Arg Leu Asn Glu Met Gly Ile Val
        435                 440                 445

Leu Glu Asp Gly Pro Gln Gly Thr Thr Trp Arg Arg Lys
    450                 455                 460

<210> SEQ ID NO 28
<211> LENGTH: 377
<212> TYPE: PRT
<213> ORGANISM: Synechocystis sp.

<400> SEQUENCE: 28

Met Lys Asn Cys Glu Asn Asp His Arg Phe Thr Thr Val Ser Ser Gly
 1               5                  10                  15

Lys Ala Trp Gly Gln Leu His Arg Phe Pro Ser Leu Ile Lys Phe Asn
            20                  25                  30

Phe Ala His Arg Ser Thr Thr Ala Met Asp Lys Pro Arg Ile Leu Ser
        35                  40                  45

Gly Val Gln Pro Thr Gly Asn Leu His Leu Gly Asn Tyr Leu Gly Ala
    50                  55                  60

Ile Arg Ser Trp Val Glu Gln Gln His Tyr Asp Asn Phe Phe Cys
65                  70                  75                  80

Val Val Asp Leu His Ala Ile Thr Val Pro His Asn Pro Gln Thr Leu
                85                  90                  95

Ala Gln Asp Thr Leu Thr Ile Ala Ala Leu Tyr Leu Ala Cys Gly Ile
            100                 105                 110

Asp Leu Gln Tyr Ser Thr Ile Phe Val Gln Ser His Val Ala Ala His
        115                 120                 125

Ser Glu Leu Ala Trp Leu Leu Asn Cys Val Thr Pro Leu Asn Trp Leu
    130                 135                 140

Glu Arg Met Ile Gln Phe Lys Glu Lys Ala Val Lys Gln Gly Glu Asn
145                 150                 155                 160

Val Ser Val Gly Leu Leu Asp Tyr Pro Val Leu Met Ala Ala Asp Ile
                165                 170                 175

Leu Leu Tyr Asp Ala Asp Lys Val Pro Val Gly Glu Asp Gln Lys Gln
            180                 185                 190

His Leu Glu Leu Thr Arg Asp Ile Val Ile Arg Ile Asn Asp Lys Phe
        195                 200                 205

Gly Arg Glu Asp Ala Pro Val Leu Lys Leu Pro Glu Pro Leu Ile Arg
    210                 215                 220

Lys Glu Gly Ala Arg Val Met Ser Leu Ala Asp Gly Thr Lys Lys Met
225                 230                 235                 240

Ser Lys Ser Asp Glu Ser Glu Leu Ser Arg Ile Asn Leu Leu Asp Pro
                245                 250                 255

Pro Glu Met Ile Lys Lys Val Lys Cys Lys Thr Asp Pro Gln
            260                 265                 270

Arg Gly Leu Trp Phe Asp Asp Pro Glu Arg Pro Glu Cys His Asn Leu
        275                 280                 285

Leu Thr Leu Tyr Thr Leu Leu Ser Asn Gln Thr Lys Glu Ala Val Ala
```

-continued

```
            290                 295                 300
Gln Glu Cys Ala Glu Met Gly Trp Gly Gln Phe Lys Pro Leu Leu Thr
305                 310                 315                 320

Glu Thr Ala Ile Ala Ala Leu Glu Pro Ile Gln Ala Lys Tyr Ala Glu
                325                 330                 335

Ile Leu Ala Asp Arg Gly Glu Leu Asp Arg Ile Ile Gln Ala Gly Asn
                340                 345                 350

Ala Lys Ala Ser Gln Thr Ala Gln Gln Thr Leu Ala Arg Val Arg Asp
                355                 360                 365

Ala Leu Gly Phe Leu Ala Pro Pro Tyr
                370                 375

<210> SEQ ID NO 29
<211> LENGTH: 419
<212> TYPE: PRT
<213> ORGANISM: Bacillus caldotenax

<400> SEQUENCE: 29

Met Asp Leu Leu Ala Glu Leu Gln Trp Arg Gly Leu Val Asn Gln Thr
  1               5                  10                  15

Thr Asp Glu Asp Gly Leu Arg Lys Leu Leu Asn Glu Glu Arg Val Thr
                 20                  25                  30

Leu Tyr Cys Gly Phe Asp Pro Thr Ala Asp Ser Leu His Ile Gly Asn
             35                  40                  45

Leu Ala Ala Ile Leu Thr Leu Arg Arg Phe Gln Gln Ala Gly His Arg
         50                  55                  60

Pro Ile Ala Leu Val Gly Gly Ala Thr Gly Leu Ile Gly Asp Pro Ser
 65                  70                  75                  80

Gly Lys Lys Ser Glu Arg Thr Leu Asn Ala Lys Glu Thr Val Glu Ala
                 85                  90                  95

Trp Ser Ala Arg Ile Lys Glu Gln Leu Gly Arg Phe Leu Asp Phe Glu
            100                 105                 110

Ala Asp Gly Asn Pro Ala Lys Ile Lys Asn Asn Tyr Asp Trp Ile Gly
            115                 120                 125

Pro Leu Asp Val Ile Thr Phe Leu Arg Asp Val Gly Lys His Phe Ser
130                 135                 140

Val Asn Tyr Met Met Ala Lys Glu Ser Val Gln Ser Arg Ile Glu Thr
145                 150                 155                 160

Gly Ile Ser Phe Thr Glu Phe Ser Tyr Met Met Leu Gln Ala Tyr Asp
                165                 170                 175

Phe Leu Arg Leu Tyr Glu Thr Glu Gly Cys Arg Leu Gln Ile Gly Gly
            180                 185                 190

Ser Asp Gln Trp Gly Asn Ile Thr Ala Gly Leu Glu Leu Ile Arg Lys
            195                 200                 205

Thr Lys Gly Glu Ala Arg Ala Phe Gly Leu Thr Ile Pro Leu Val Thr
        210                 215                 220

Lys Ala Asp Gly Thr Lys Phe Gly Lys Thr Glu Ser Gly Thr Ile Trp
225                 230                 235                 240

Leu Asp Lys Glu Lys Thr Ser Pro Tyr Glu Phe Tyr Gln Phe Trp Ile
                245                 250                 255

Asn Thr Asp Asp Arg Asp Val Ile Arg Tyr Leu Lys Tyr Phe Thr Phe
            260                 265                 270

Leu Ser Lys Glu Glu Ile Glu Ala Leu Glu Gln Glu Leu Arg Glu Ala
        275                 280                 285
```

```
-continued

Pro Glu Lys Arg Ala Ala Gln Lys Ala Leu Ala Glu Glu Val Thr Lys
    290                 295                 300

Leu Val His Gly Glu Glu Ala Leu Arg Gln Ala Ile Arg Ile Ser Glu
305             310                 315                 320

Ala Leu Phe Ser Gly Asp Ile Ala Asn Leu Thr Ala Ala Glu Ile Glu
                325                 330                 335

Gln Gly Phe Lys Asp Val Pro Ser Phe Val His Glu Gly Gly Asp Val
            340                 345                 350

Pro Leu Val Glu Leu Leu Val Ser Ala Gly Ile Ser Pro Ser Lys Arg
        355                 360                 365

Gln Ala Arg Glu Asp Ile Gln Asn Gly Ala Ile Tyr Val Asn Gly Glu
    370                 375                 380

Arg Leu Gln Asp Val Gly Ala Ile Leu Thr Ala Glu His Arg Leu Glu
385                 390                 395                 400

Gly Arg Phe Thr Val Ile Arg Arg Gly Lys Lys Lys Tyr Tyr Leu Ile
                405                 410                 415

Arg Tyr Ala
```

PLANT AMINOACYL-TRNA SYNTHETASE

This application claims the benefit of U.S. Provisional Application No. 60/092,866, filed Jul. 15, 1998.

FIELD OF THE INVENTION

This invention is in the field of plant molecular biology. More specifically, this invention pertains to nucleic acid fragments encoding aminoacyl-tRNA synthetase in plants and seeds.

BACKGROUND OF THE INVENTION

All tRNAs have two functions: to chemically link to a specific amino acid and to recognize a codon in mRNA so that the linked amino acid can be added to a growing peptide chain during protein synthesis. In general there is at least one aminoacyl-tRNA synthetase for each of the twenty amino acids. A specific aminoacyl-tRNA synthetase links an amino acid to the 2' or 3' hydroxyl of the adenosine residue at the 3'-terminus of a tRNA molecule. Once its correct amino acid is attached, a tRNA then recognizes a codon in mRNA, thus deliverng its amino acid to the growing polypeptide chain. These enzymatic functions are critical to gene expression (Neidhart et al. (1975) *Annu. Rev. Microbiol.* 29:215–250). Mutations in tRNA synthetases often result in alterations in protein synthesis and in some cases cell death.

Plants like other cellular organisms have aminoacyl-tRNA synthetases. However a complete description of the plant 'complement' of aminoacyl-tRNA synthetases has not been published. It is anticipated that plants will likely have at least forty aminoacyl-tRNA synthetases. Plants have three sites of protein synthesis: the cytoplasm, the mitochondria and the chloroplast. Accordingly, there could be as many as sixty aminoacyl-tRNA synthetases. Based on knowledge of other eukaryotes the cytoplasmic and mitochondrial aminoacyl-tRNA synthetases are expected to be encoded by the same gene. This gene should be nuclearly encoded and produce two alternate products, one with a mitochondrial specific transit peptide, and the other without this targeting signal. The chloroplast is the other site of protein synthesis in plants. Based on a few examples of known plant chloroplast specific aminoacyl-tRNA synthetase genes it appears that these genes are also nuclear-encoded. Chloroplast aminoacyl-tRNA synthetases are directed to the chloroplast by a transit peptide.

Because of the central role aminoacyl-tRNA synthetases play in protein synthesis any agent that inhibits or disrupts aminoacyl-tRNA synthetase activity is likely to be toxic. Indeed a number of aminoacyl-tRNA synthetase inhibitors (antibiotics and herbicides) are known (Zon et al. (1988) *Phytochemishy* 27(3):711–714 and Heacock et al. (1996) *Bioorganic Chemistry* 24(3):273–289). Thus it may be possible to develop new herbicides that target arinoacyl-tRNA synthetases and engineer aminoacyl-tRNA synthetases that are resistant to such herbicides. Accordingly, the availability of nucleic acid sequences encoding all or a portion of these enzymes would facilitate studies to better understand protein synthesis in plants, provide genetic tools for the manipulation of gene expression, and provide a possible target for herbicides.

SUMMARY OF THE INVENTION

The instant invention relates to isolated nucleic acid fragments encoding aminoacyl-tRNA synthetase. Specifically, this invention concerns an isolated nucleic acid fragment encoding an aspartyl-tRNA synthetase, cysteinyl-tRNA synthetase, tryptophanyl-tRNA synthetase or tyrosyl-tRNA synthetase and an isolated nucleic acid fragment that is substantially similar to an isolated nucleic acid fragment encoding an aspartyl-tRNA synthetase, cysteinyl-tRNA synthetase, tryptophanyl-tRNA synthetase or tyrosyl-tRNA synthetase. In addition, this invention relates to a nucleic acid fragment that is complementary to the nucleic acid fragment encoding aspartyl-tRNA synthetase, cysteinyl-tRNA synthetase, tryptophanyl-tRNA synthetase or tyrosyl-tRNA synthetase.

An additional embodiment of the instant invention pertains to a polypeptide encoding all or a substantial portion of an aminoacyl-tRNA synthetaseselected from the group consisting of aspartyl-tRNA synthetase, cysteinyl-tRNA synthetase, tryptophanyl-tRNA synthetase and tyrosyl-tRNA synthetase.

In another embodinent, the instant invention relates to a chimeric gene encoding an aspartyl-tRNA synthetase, cysteinyl-tRNA synthetase, tryptophanyl-tRNA synthetase or tyrosyl-tRNA synthetase, or to a chimeric gene that comprises a nucleic acid fragment that is complementary to a nucleic acid fragment encoding an aspartyl-tRNA synthetase, cysteinyl-tRNA synthetase, tryptophanyl-tRNA synthetase or tyrosyl-tRNA synthetase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding an aspartyl-tRNA synthetase, cysteinyl-tRNA synthetase, tryptophanyl-tRNA synthetase or tyrosyl-tRNA synthetase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of an aspartyl-tRNA synthetase, cysteinyl-tRNA synthetase, tryptophanyl-tRNA synthetase or tyrosyl-tRNA synthetase in a transformed host cell comprising: a) transforming a host cell with a chimeric gene comprising a nucleic acid fragment encoding an aspartyl-tRNA synthetase, cysteinyl-tRNA synthetase, tryptophanyl-tRNA synthetase or tyrosyl-tRNA synthetase; and b) growing the transformed host cell under conditions that are suitable for expression of the chimeric gene wherein expression of the chimeric gene results in production of altered levels of aspartyl-tRNA synthetase, cysteinyl-tRNA synthetase, tryptophanyl-tRNA synthetase or tyrosyl-tRNA synthetase in the transformed host cell.

An addition embodiment of the instant invention concerns a method for obtaining a nucleic acid fragment encoding all or a substantial portion of an amino acid sequence encoding an aspartyl-tRNA synthetase, cysteinyl-tRNA synthetase, tryptophanyl-tRNA synthetase or tyrosyl-tRNA synthetase.

A further embodiment of the instant invention is a method for evaluating at least one compound for its ability to inhibit the activity of an aspartyl-tRNA synthetase, cysteinyl-tRNA synthetase, tryptophanyl-tRNA synthetase or tyrosyl-tRNA synthetase, the method comprising the steps of: (a) transforming a host cell with a chimeric gene comprising a nucleic acid fragment encoding an aspartyl-tRNA synthetase, cysteinyl-tRNA synthetase, tryptophanyl-tRNA synthetase or tyrosyl-tRNA synthetase, operably linked to suitable regulatory sequences; (b) growing the transformed host cell under conditions that are suitable for expression of the chimeric gene wherein expression of the chimeric gene results in production of aspartyl-tRNA synthetase, cysteinyl-tRNA synthetase, tryptophanyl-tRNA synthetase or tyrosyl-tRNA synthetase in the transformed host cell; (c) optionally purifing the aspartyl-tRNA synthetase, cysteinyl-tRNA synthetase, tryptophanyl-tRNA synthetase or tyrosyl-tRNA synthetase expressed by the transformed host cell; (d) treating the aspartyl-tRNA synthetase, cysteinyl-tRNA synthetase, tryptophanyl-tRNA synthetase or tyrosyl-tRNA synthetase with a compound to be tested; and (e) comparing the activity of the aspartyl-tRNA synthetase, cysteinyl-tRNA synthetase, tryptophanyl-tRNA synthetase or tyrosyl-tRNA synthetase that has been treated with a test compound to the activity of an untreated aspartyl-tRNA synthetase, cysteinyl-tRNA synthetase, tryptophanyl-tRNA synthetase or tyrosyl-tRNA synthetase, thereby selecting compounds with potential for inhibitory activity.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the

TABLE 1

Aninoacyl-tRNA Synthetase

| Protein | Clone Designation | SEQ ID NO: (Nucleotide) | (Amino Acid) |
|---|---|---|---|
| Aspartyl-tRNA Synthetase | p0094.cssth73r | 1 | 2 |
| Aspartyl-tRNA Synthetase | r10n.pk0015.g11 | 3 | 4 |
| Aspartyl-tRNA Synthetase | sf11.pk0046.e8 | 5 | 6 |
| Aspartyl-tRNA Synthetase | wleln.pk0021.e6 | 7 | 8 |
| Cysteinyl-tRNA Synthetase | p0119.cmtmt52r | 9 | 10 |
| Cysteinyl-tRNA Synthetase | rs11n.pk016.p18 | 11 | 12 |
| Cysteinyl-tRNA Synthetase | sf11.pk0013.f9 | 13 | 14 |
| Tryptophanyl-tRNA Synthetase | p0118.chsb187r | 15 | 16 |
| Tryptophanyl-tRNA Synthetase | sdp4c.pk033.n11 | 17 | 18 |
| Tryptophanyl-tRNA Synthetase | wlm4.pk0013.c12 | 19 | 20 |
| Tyrosyl-tRNA Synthetase | cs1.pk0035.d2 | 21 | 22 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6X SSC, 0.5% SDS at room temperature for 15 min, then repeated with 2X SSC, 0.5% SDS at 45° C. for 30 min, and then repeated twice with 0.2X SSC, 0.5% SDS at 50° C. for 30 min. A more preferred set of stringent conditions uses higher temperatures in which the washes are identical to those above except for the temperature of the final two 30 min washes in 0.2x SSC, 0.5% SDS was increased to 60° C. Another preferred set of highly stringent conditions uses two final washes in 0.1X SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASAR-GENE bioinformatics computing suite (DNASTAR Inc., Madison, Wis.). Multiple alignment of the sequences was performed using the Clustal method of aligmnent (Higgins and Sharp (1989) CABIOS 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5'non-coding sequences), within, or downstream (3'non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning. A Laboratory Manual*; Cold Spring Harbor Laboratory Press: Cold Spring Harbor, 1989 (hereinafter "Maniatis").

Nucleic acid fragments encoding at least a portion of several aninoacyl-tRNA synthetases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other aspartyl-tRNA synthetase, cysteinyl-tRNA synthetase, tryptophanyl-tRNA synthetase or tyrosyl-tRNA synthetase enzymes, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of aminoacyl-tRNA synthetase activity in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.*100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of nmicrobial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded aninoacyl-tRNA synthetase. An example of a vector for high level expression of the instant polypeptides in a bacterial host is provided (Example 9).

Additionally, the instant polypeptides can be used as a targets to facilitate design and/or identification of inhibitors of those enzymes that may be usefull as herbicides. This is desirable because the polypeptides described herein catalyze various steps in protein synthesis. Accordingly, inhibition of the activity of one or more of the enzymes described herein could lead to inhibition plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defmed genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 1 7:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean and wheat tissues were prepared. The characteristics of the libraries are described below.

TABLE 2 cDNA Libraries from Corn, Rice, Soybean and Wheat

| Library | Tissue | Clone |
|---|---|---|
| cs1 | Corn leaf sheath from 5 week old plant | cs1.pk0035.d2 |
| p0094 | Corn ear leaf sheath, 2–3 weeks after pollen shed* | p0094.cssth73r |
| p0118 | Corn pooled stem tissue from the 4–5 internodes subtending the tassel, V8–V12 stages* | p0118.chsb187r |
| p0119 | Corn ear shoot/w husk: V-12 stage* | p0119.cmtmt52r |
| r10n | Rice 15 day old leaf* | r10n.pk0015.g11 |
| rs11n | Rice 15 day old seedling* | rs11n.pk016.p18 |
| sdp4c | Soybean developing embryo (9–11 mm) | sdp4c.pk033.n11 |
| sf11 | Soybean immature flower | sf11.pk0013.f9 |
|  |  | sf11.pk0046.e8 |
| wle1n | Wheat leaf from 7 day old etiolated seedling* | wle1n.pk0021.e6 |
| wlm4 | Wheat seedlings 4 hours after treatment with a fungicide** | wlm4.pk0013.c12 |

*These libraries were normalized essentially as described in U.S. Pat. No. 5,482,845, incorporated herein by reference.
**Fungicide Application of 6-iodo-2-propoxy-3 -propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP* XR vectors according to the manufacturer's protocol (Stratagene Cloning Systems, La Jolla, Calif.). The Uni-ZAP* XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding aninoacyl-tRNA synthetases were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Aspartyl-tRNA Synthetase

The BLASTX search using the EST sequences from clones listed in Table 3 revealed similarity of the polypeptides encoded by the cDNAs to aspartyl-tRNA synthetase from *Drosophila melanogaster* (NCBI Identifier No. gi 4512034), *Rattus norvegicus* (NCBI Identifier No. gi 135099) and *Homo sapiens* (NCBI Identifier no. gi 4557513). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Drosophila melanogaster, Rattus norvegicus* and *Homo sapiens* Aspartyl-tRNA Synthetase

| Clone | Status | BLAST pLog Score |
|---|---|---|
| p0094.cssth73r | FIS | 134.00 (gi 4512034) |
| r10n.pk0015.g11 | FIS | 51.15 (gi 135099) |
| sf11.pk0046.e8 | FIS | 102.00 (gi 4557513) |
| w1e1n.pk0021.e6 | FIS | 21.40 (gi 4557513) |

The data in Table 4 represents a calculation of the percent identity of the amino acid sequences set forth in SEQ ID NOs:2, 4, 6 and 8 and the *Drosophila melanogaster, Rattus norvegicus* and *Homo sapiens* aspartyl-tRNA synthetase sequences (SEQ ID NOs:23, 24 and 25 respectively).

TABLE 4

Percent Identity of Amino Acid Sequences Deduced From the Nucleotide Sequences of cDNA Clones Encoding Polypeptides Homologous to *Drosophila melanogaster, Rattus norvegicus* and *Homo sapiens* Aspartyl-tRNA Synthetase

| SEQ ID NO. | Percent Identity to |
|---|---|
| 2 | 51% (gi 4512034) |
| 4 | 65% (gi 135099) |
| 6 | 51% (gi 4557513) |
| 8 | 52% (gi 4557513) |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of an aspartyl-tRNA synthetase. These sequences represent the first corn, rice, soybean and wheat sequences encoding aspartyl-tRNA synthetase.

Example 4

Characterization of cDNA Clones Encoding Cysteinyl-tRNA Synthetase

The BLASTX search using the EST sequences from clones listed in Table 5 revealed similarity of the polypeptides encoded by the cDNAs to cysteinyl-tRNA synthetase from *Haemophilus influenzae* (NCBI Identifier No. gi 1174501) and *Escherichia coli* (NCBI Identifier No. gi 41203). Shown in Table 5 are the BLAST results for individual ESTs ("EST"), the sequences of the entire cDNA inserts comprising the indicated cDNA clones ("FIS"), or contigs assembled from two or more ESTs ("Contig"):

TABLE 5

BLAST Results for Sequences Encoding Polypeptides Homologous to *Haemophilus influenzae* and *Escherichia coli* Cysteinyl-tRNA Synthetase

| Clone | Status | BLAST pLog Score |
|---|---|---|
| p0119.cmtmt52r | FIS | 104.00 (gi 1174501) |
| rs11n.pk016.p18 | FIS | 108.00 (gi 41203) |
| sf11.pk0013.f9 | FIS | 117.00 (gi 1174501) |

The data in Table 6 represents a calculation of the percent identity of the amino acid sequences set forth in SEQ ID NOs: 10, 12 and 14 and the *Haemophilus influenzae* and *Escherichia coli* sequences (SEQ ID NOs:26 and 27 respectively).

TABLE 6

Percent Identity of Amino Acid Sequences Deduced From the Nucleotide Sequences of cDNA Clones Encoding Polypeptides Homologous to *Haemophilus influenzae* and *Escherichia coli* Cysteinyl-tRNA Synthetase

| SEQ ID NO. | Percent Identity to |
|---|---|
| 10 | 43% (gi 1174501) |
| 12 | 44% (gi 41203) |
| 14 | 44% (gi 1174501) |

Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a cysteinyl-tRNA synthetase. These sequences represent the first corn, rice and soybean sequences encoding cysteinyl-tRNA synthetase.

Example 5

Characterization of cDNA Clones Encoding Tryptophanyl-tRNA Synthetase

The BLASTX search using the EST sequences from clones listed in Table 7 revealed similarity of the polypeptides encoded by the cDNAs to tryptophanyl-tRNA synthetase from Synechocystis sp. (NCBI Identifier No. gi 2501072). Shown in Table 7 are the BLAST results for individual ESTs ("EST"), the sequences of the entire cDNA inserts comprising the indicated cDNA clones ("FIS"), or contigs assembled from two or more ESTs ("Contig"):

TABLE 7

BLAST Results for Sequences Encoding Polypeptides Homologous to *Synechocystis sp.* Tryptophanyl-tRNA Synthetase

| Clone | Status | BLAST pLog Score to (gi 2501072) |
|---|---|---|
| p0118.chsb187r | EST | 104.00 |
| sdp4c.pk033.n11 | FIS | 103.00 |
| w1m4.pk0013.c12 | FIS | 43.22 |

The data in Table 8 represents a calculation of the percent identity of the amino acid sequences set forth in SEQ ID NOs: 16, 18 and 24 and the Synechocystis sp. sequence (SEQ ID NO:28).

TABLE 8

Percent Identity of Amino Acid Sequences Deduced From the Nucleotide Sequences of cDNA Clones Encoding Polypeptides Homologous to *Synechocystis sp.* Tryptophanyl-tRNA Synthetase

| SEQ ID NO. | Percent Identity to (gi 2501072) |
|---|---|
| 16 | 49% |
| 18 | 50% |
| 20 | 51% |

Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a tryptophanyl-tRNA synthetase. These sequences represent the first corn, soybean and wheat sequences encoding tryptophanyl-tRNA synthetase.

Example 6

Characterization of cDNA Clones Encoding Tyrosyl-tRNA Synthetase

The BLASTX search using the EST sequence from the clone listed in Table 9 revealed similarity of the polypeptide encoded by the cDNA to tyrosyl-tRNA synthetase from *Bacillus caldotenax* (NCBI Identifier No. gi 135196). Shown in Table 9 are the BLAST results for the sequence of the entire cDNA insert comprising the indicated cDNA clone ("FIS"):

TABLE 9

BLAST Results for Sequences Encoding Polypeptides Homologous to *Bacillus caldotenax* Tyrosyl-tRNA Synthetase

| Clone | Status | BLAST pLog Score to (gi 135196) |
|---|---|---|
| cs1.pk0035.d2 | FIS | 62.52 |

The data in Table 10 represents a calculation of the percent identity of the amino acid sequence set forth in SEQ ID NO:22 the *Bacillus caldotenax* sequence (SEQ ID NO:29).

TABLE 10

Percent Identity of Amino Acid Sequences Deduced From the Nucleotide Sequences of cDNA Clones Encoding Polypeptides Homologous to *Bacillus caldetenax* Tyrosyl-tRNA Synthetase

| SEQ ID NO. | Percent Identity to (gi 135196) |
|---|---|
| 22 | 52% |

Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10 , GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a tyrosyl-tRNA synthetase. This sequence represent the first corn sequence encoding tyrosyl-tRNA synthetase.

Example 7

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 8

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean tnansformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL CaCl$_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 10

Evaluating Compounds for Their Ability to Inhibit the Activity of Aminoacyl-tRNA Synthetase The polypeptides described herein may be produced using any number of methods known to those skilled in the art.

Such methods include, but are not limited to, expression in bacteria as described in Example 9, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Conmmon fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fuision protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for aminoacyl-tRNA synthetases are presented by Zon et al. (1988) *Phytochemistry* 27(3):711–714 and Heacock et al. (1996) *Bioorganic Chemistry* 24(3): 273–289.

What is claimed is:

1. An isolated polynucleotide comprising:
   (a) a nucleotide sequence encoding an aspartyl-tRNA synthetase, wherein the amino acid sequence of the synthetase and the amino acid sequence of SEQ ID NO:2 have at least 80% identity based on the Clustal alignment method, or
   (b) the complement of the nucteotide sequence of (a).

2. The polynucleotide of claim 1, wherein the amino acid sequence of the synthetase and the amino acid sequence of SEQ ID NO:2 have at least 90% identity based on the Clustal alignment method.

3. The polynucleotide of claim 1, wherein the amino acid sequence of the synthetase and the amino acid sequence of SEQ ID NO:2 have at least 95% identity based on the Clustal alignment method.

4. The polynucleotide of claim 1, wherein the synthetase comprises the amino acid sequence of SEQ ID NO:2.

5. The polynucleotide of claim 1 comprising the nucleotide sequence of SEQ ID NO:1.

6. A chimeric gene comprising the polynucleotide of claim 1 operably linked to a regulatory sequence.

7. A method for transforming a cell comprising transforming a cell with the polynucleotide of claim 1.

8. A cell comprising the chimeric gene of claim 6.

9. A method for producing a plant comprising transforming a plant cell with the polynucleotide of claim 1 and regenerating a plant from the transformed plant cell.

10. A plant comprising the chimeric gene of claim 6.

11. A seed comprising the chimeric gene of claim 6.

12. An isolated polynucleotide consisting of:
   (a) a nucleotide sequence encoding a polypeptide, wherein the amino acid sequence of the polypeptide is the amino acid sequencc of SEQ ID NO:4, SEQ ID NO:6, or SEQ ID NO:8, or
   (b) the complement of the nucleotide sequence of (a).

13. The polynucleotide of claim 12 consisting of the nucleotide sequence of SEQ ID NO:3, SEQ ID NO:5, or SEQ ID NO:7.

14. A chimeric gene comprising the polynucleotide of claim 12 operably linked to a regulatory sequence.

15. A method for transforming a cell comprising transforming a cell with the polynucleotide of claim 12.

16. A cell comprising the chimeric gene of claim 14.

* * * * *